United States Patent
Soles et al.

(10) Patent No.: US 8,977,507 B2
(45) Date of Patent: Mar. 10, 2015

(54) EVENT DETECTION SYSTEM USER INTERFACE SYSTEM COUPLED TO MULTIPLE SENSORS INCLUDING AN IMPACT DETECTION SYSTEM

(75) Inventors: Alexander M. Soles, Bloomington, IN (US); Matthew R. Walsh, Westfield, IN (US); Eric B. Scott, Heltonville, IN (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 744 days.

(21) Appl. No.: 13/161,974

(22) Filed: Jun. 16, 2011

(65) Prior Publication Data

US 2012/0191374 A1 Jul. 26, 2012

Related U.S. Application Data

(60) Provisional application No. 61/435,255, filed on Jan. 21, 2011.

(51) Int. Cl.
*G01B 5/28* (2006.01)
*F41H 5/20* (2006.01)
(Continued)

(52) U.S. Cl.
CPC ............... *G06F 7/00* (2013.01); *G08B 13/126* (2013.01); *F41H 5/007* (2013.01); *F41H 5/24* (2013.01);
(Continued)

(58) Field of Classification Search
CPC ..... G01N 2291/106; F41H 5/013; F41H 5/04; F41H 5/0471; F41H 5/007; F41H 5/023; F41H 5/0414; F41H 5/0485; F41H 5/0492; F41H 5/16; F41H 5/18; F41H 5/20; F41H 1/02; F41H 7/02; F41H 7/00; G01M 5/0033; G01M 5/0066

USPC ........... 702/36, 35, 39, 41–44, 57, 59, 65, 81, 702/84, 108, 116, 127, 139–140, 182–183, 702/185, 189; 73/866.3; 324/693, 691; 404/71; 89/36.01–36.05, 36.13, 901, 89/904, 906, 918–919, 922, 929, 935, 89/937; 345/55, 156, 170, 174–175, 177, 345/207, 690, 697

See application file for complete search history.

(56) References Cited

U.S. PATENT DOCUMENTS 3,602,088 A * 8/1971 Spring .......................... 89/36.13
5,516,113 A 5/1996 Hodge
(Continued)

FOREIGN PATENT DOCUMENTS

WO WO 2009/102310 8/2009

OTHER PUBLICATIONS

BBN Technologies, "Boomerang Position and Heading Sensor," at least as early as Jan. 8, 2011, 1 pg.
(Continued)

*Primary Examiner* — Toan Le
(74) *Attorney, Agent, or Firm* — Christopher A. Monsey

(57) ABSTRACT

A damage detection and remediation system includes a sensing device for detecting damage events related to a structure of interest. Such damage events may include impact from a ballistic object, a tamper event, a physical impact, or other events that may affect structural integrity or cause failure. Illustratively, the sensing device is in communication with a measurement system to determine damage criteria, and a processing system which is configured to use the damage criteria to determine, for example, a direction of the initiation point of a ballistic causing the damage event.

6 Claims, 25 Drawing Sheets

(51) Int. Cl.
  *G09G 3/20* (2006.01)
  *G06F 7/00* (2006.01)
  *G08B 13/12* (2006.01)
  *F41H 5/007* (2006.01)
  *F41H 5/24* (2006.01)
  *F41H 7/02* (2006.01)
  *F41J 5/04* (2006.01)
  *G01M 5/00* (2006.01)
  *H05K 13/00* (2006.01)

(52) U.S. Cl.
  CPC . *F41H 7/02* (2013.01); *F41J 5/041* (2013.01); *G01M 5/0033* (2013.01); *G01M 5/0066* (2013.01); *G01M 5/0091* (2013.01); *H05K 13/00* (2013.01)
  USPC .............................. 702/36; 89/36.13; 345/55

(56) References Cited

U.S. PATENT DOCUMENTS

| | | | |
|---|---|---|---|
| 5,586,086 A | 12/1996 | Permuy et al. | |
| 5,831,936 A | 11/1998 | Zlotnick et al. | |
| H1916 H | 11/2000 | Hollander | |
| 6,239,747 B1 | 5/2001 | Kaminski | |
| 6,903,676 B1 | 6/2005 | Frady et al. | |
| 7,049,998 B1 | 5/2006 | Frady et al. | |
| 7,207,566 B2 | 4/2007 | Hodge | |
| 7,233,546 B2 | 6/2007 | Berkovich et al. | |
| 7,409,899 B1 | 8/2008 | Beekman | |
| 7,765,083 B2 | 7/2010 | Zank et al. | |
| 7,855,935 B1 | 12/2010 | Lauder et al. | |
| 7,954,359 B1 | 6/2011 | Paderewski et al. | |
| 8,046,177 B2 | 10/2011 | Liu et al. | |
| 8,149,156 B1 * | 4/2012 | Allred et al. | 342/52 |
| 8,265,889 B2 | 9/2012 | Qing et al. | |
| 2006/0042396 A1 | 3/2006 | Qing et al. | |
| 2006/0053534 A1 | 3/2006 | Mullen | |
| 2006/0079747 A1 | 4/2006 | Beard et al. | |
| 2007/0018083 A1 | 1/2007 | Kumar et al. | |
| 2007/0213943 A1 | 9/2007 | Curry et al. | |
| 2007/0260407 A1 | 11/2007 | Van Albert et al. | |
| 2007/0273165 A1 | 11/2007 | Beck et al. | |
| 2008/0034954 A1 * | 2/2008 | Grober | 89/41.05 |
| 2008/0129499 A1 | 6/2008 | Masuzaka | |
| 2008/0129982 A1 | 6/2008 | Nakamura et al. | |
| 2008/0312846 A1 | 12/2008 | Kessler et al. | |
| 2009/0027229 A1 * | 1/2009 | Fortson et al. | 340/870.07 |
| 2009/0192727 A1 | 7/2009 | Ford | |
| 2009/0194942 A1 | 8/2009 | Hodge | |
| 2009/0241636 A1 | 10/2009 | Obori | |
| 2009/0301198 A1 | 12/2009 | Sohn et al. | |
| 2009/0326834 A1 | 12/2009 | Sundaresan et al. | |
| 2010/0083733 A1 | 4/2010 | Russell et al. | |
| 2010/0127133 A1 | 5/2010 | Schrevere et al. | |
| 2011/0030537 A1 | 2/2011 | Mullen | |
| 2011/0050258 A1 | 3/2011 | Katazawa et al. | |
| 2011/0089958 A1 * | 4/2011 | Malecki et al. | 324/693 |
| 2011/0210737 A1 | 9/2011 | Tseitlin et al. | |
| 2011/0222225 A1 | 9/2011 | Kessler et al. | |
| 2011/0231112 A1 | 9/2011 | Soejima et al. | |
| 2012/0001027 A1 | 1/2012 | Jones et al. | |
| 2012/0059600 A1 | 3/2012 | Xiang et al. | |
| 2012/0197482 A1 | 8/2012 | Moser et al. | |

OTHER PUBLICATIONS

BBN Technologies, "Boomerang Perimeter Defense," at least as early as Jan. 8, 2011, 1 pg.
BBN Technologies, "Indispensable for Force Protection," 2009, 3 pgs., downloaded from http://boomerang.bbn.com.

* cited by examiner

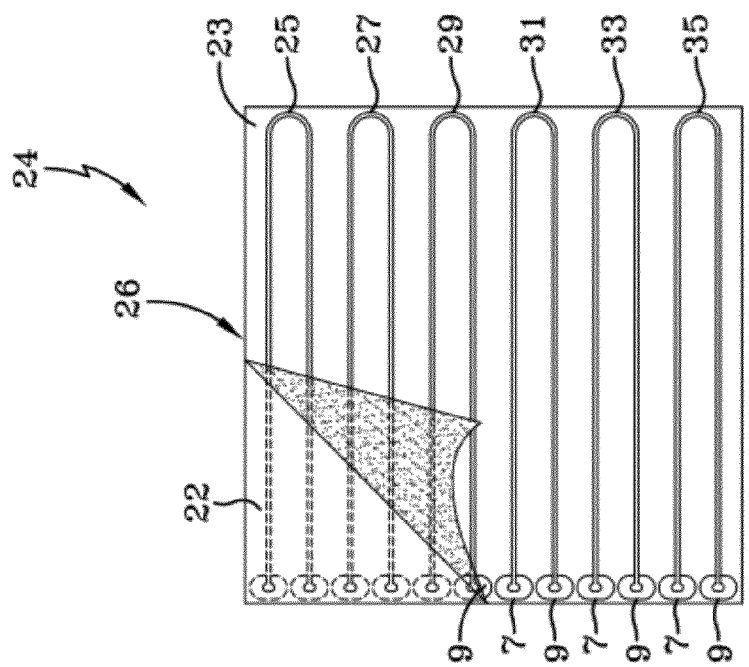
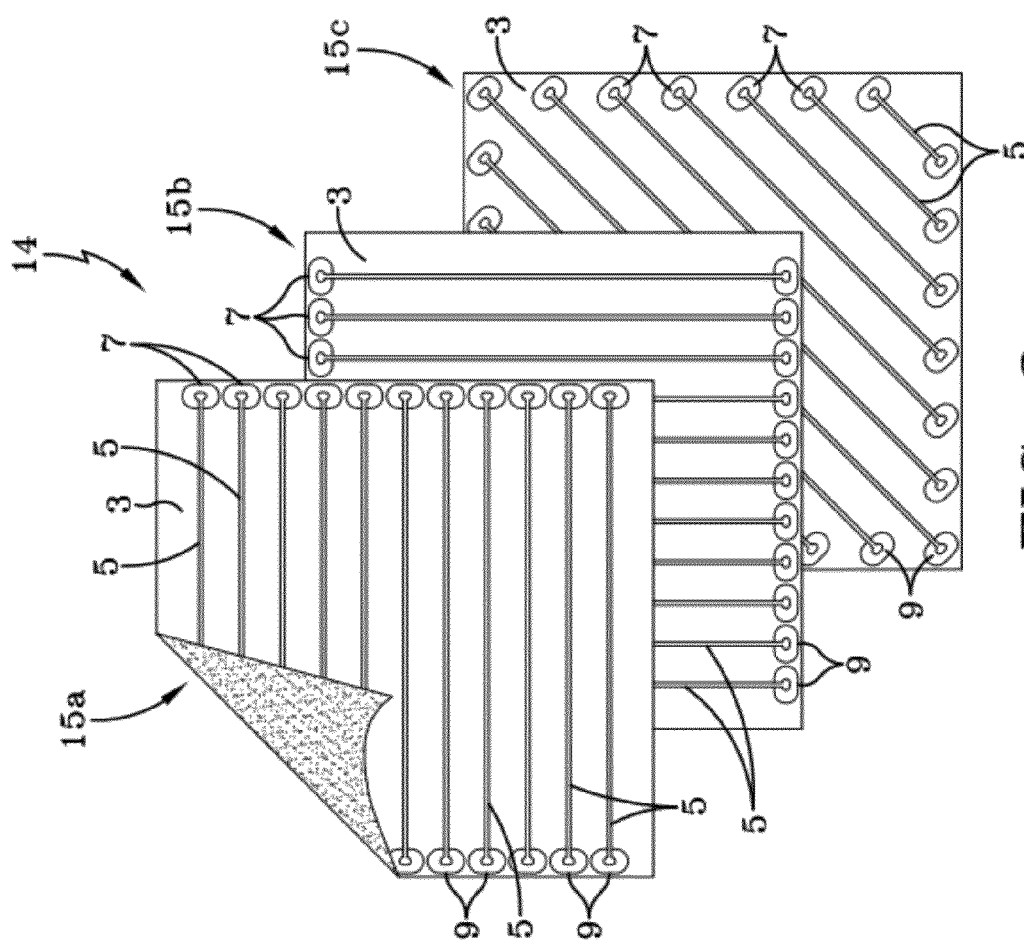

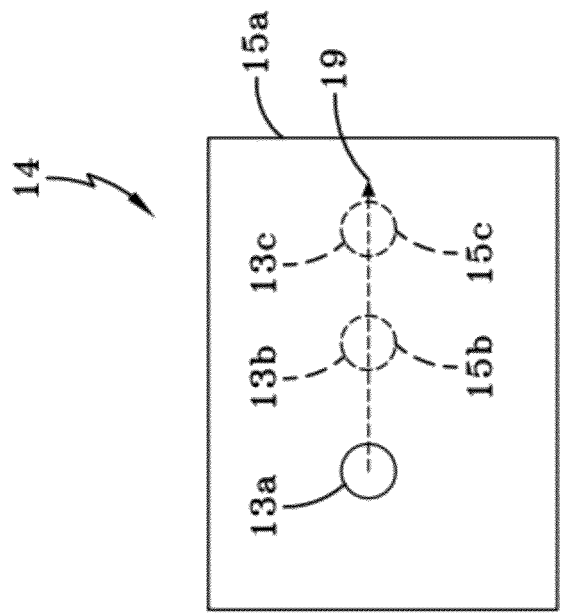
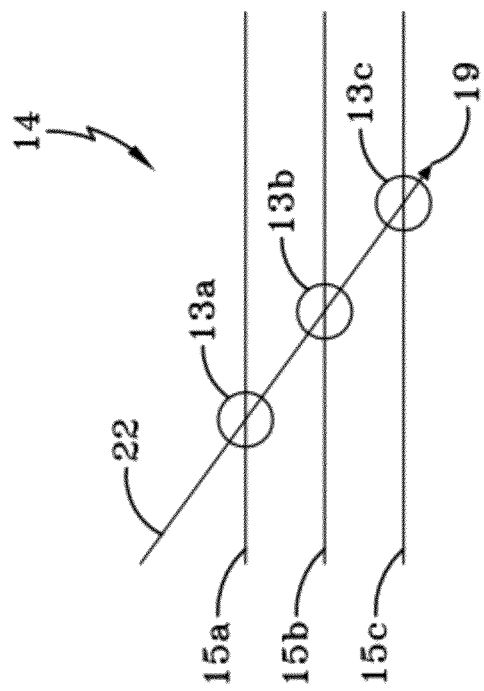

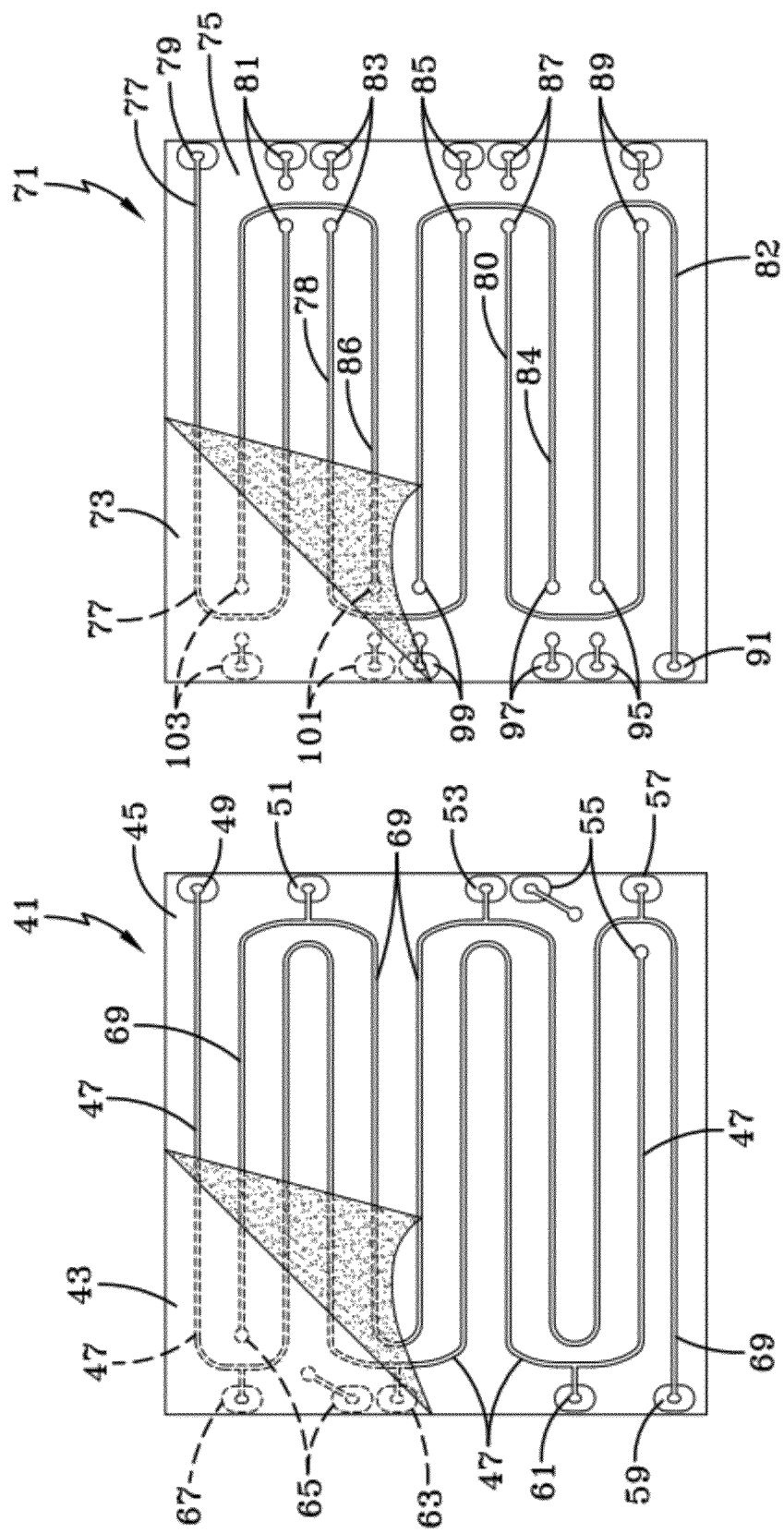

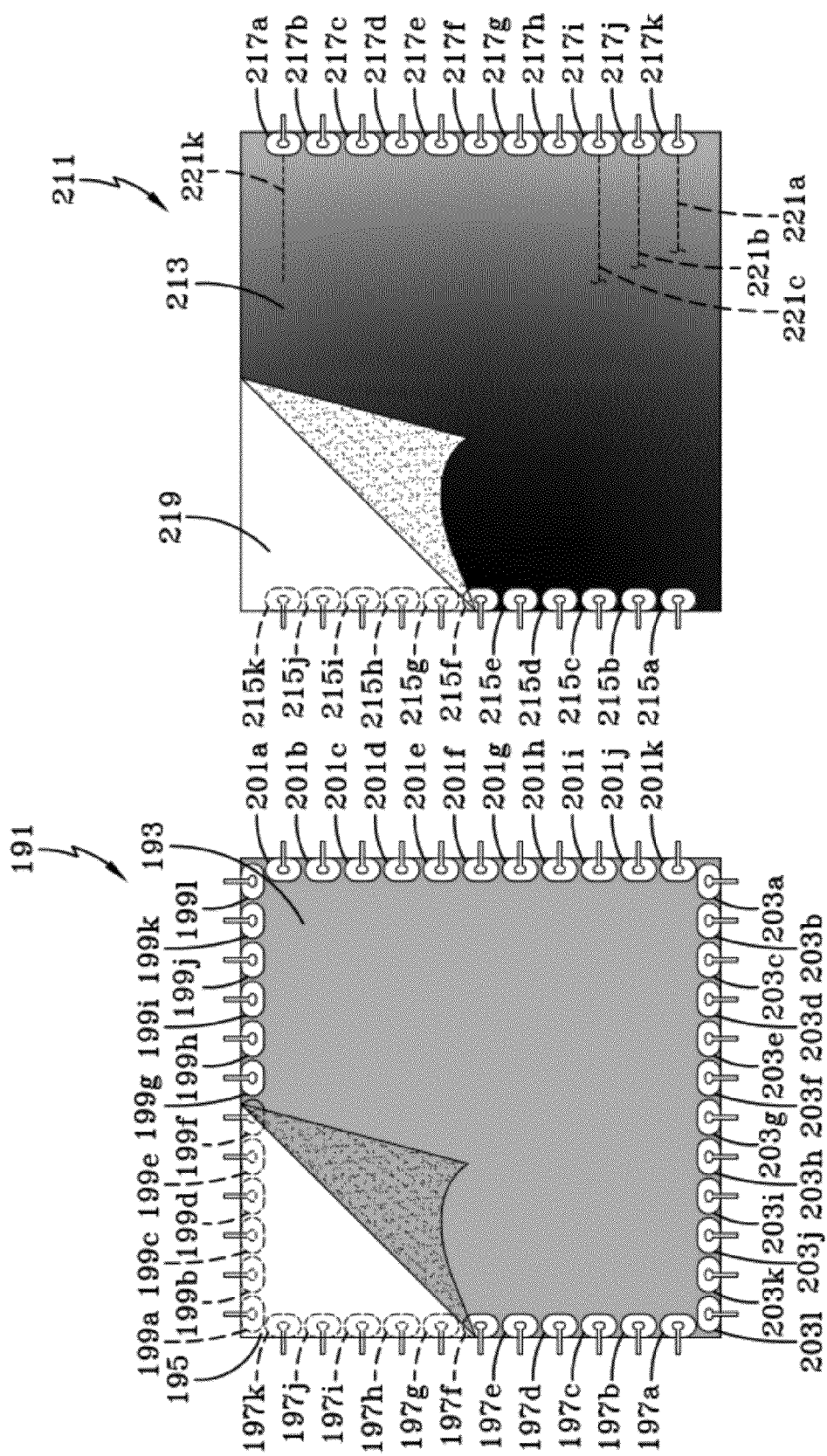

EVENT DETECTION SYSTEM USER INTERFACE SYSTEM COUPLED TO MULTIPLE SENSORS INCLUDING AN IMPACT DETECTION SYSTEM

CROSS-REFERENCE TO RELATED APPLICATION

This application claims priority to U.S. Provisional Patent Application Ser. No. 61/435,255, filed Jan. 21, 2011, the disclosure of which is expressly incorporated by reference herein. The present application is also related to U.S. patent application Ser. No. 13/161,965, filed Jun. 16, 2011, entitled "VEHICLE DAMAGE DETECTION SYSTEM", now U.S. Pat. No. 8,788,220, U.S. patent application Ser. No. 13/161,968, filed Jun. 16, 2011, entitled "EVENT DETECTION SYSTEM HAVING MULTIPLE SENSOR SYSTEMS IN COOPERATION WITH AN IMPACT DETECTION SYSTEM", now U.S. Pat. No. 8,788,218, U.S. patent application Ser. No. 13/161,984, filed Jun. 16, 2011, entitled "EVENT DETECTION CONTROL SYSTEM FOR OPERATING A REMOTE SENSOR OR PROJECTILE SYSTEM", and U.S. patent application Ser. No. 13/161,935, filed Jun. 16, 2011, entitled "DAMAGE DETECTION AND REMEDIATION SYSTEM AND METHODS THEREOF", the disclosures of which are expressly incorporated by reference herein.

STATEMENT REGARDING FEDERALLY SPONSORED RESEARCH OR DEVELOPMENT

The invention described herein was made in the performance of official duties by employees of the Department of the Navy and may be manufactured, used and licensed by or for the United States Government for any governmental purpose without payment of any royalties thereon.

FIELD OF THE INVENTION

The present invention relates to a system and apparatus for detecting events of interest, such as damage events associated with impacts, interactions between structures, or structural integrity events for which detection is desired.

BACKGROUND AND SUMMARY OF THE INVENTION

Current structures such as armor, microelectronics, or critical infrastructure systems lack effective, real-time sensing systems to detect damage events of interest, such as an impact from a ballistic object, a tamper event, a physical impact such as from debris (such as airborne or space debris), or other damage events which may affect structural integrity or cause failure.

Detection of armor or surface failures may be currently based on aural indications or manual inspection after an event which could be delayed due to ongoing use of equipment or operations. When a critical armor or surface element becomes compromised, lives may be placed at risk. Currently, there is no known way of effectively detecting these failures immediately or as the event happens.

Security forces, emergency response, or law enforcement personnel often rely on body armor and personal protective equipment. Due to designs of such armor or equipment, users cannot reliably predict where a potential armor or equipment failure is occurring, or if the armor or equipment has been compromised to the point of potential failure.

Traditionally, medics and emergency response personnel must manually inspect a victim for ballistic wounds that have occurred from damage events, such as bomb blasts or gunfire. They can only perform and make an assessment based on visible injuries, such as a penetration wound.

Space based systems also lack effective detection systems which meet requirements for space launch, such as liftoff and other constraints. For example, onboard the international space station, astronauts and ground controllers do not know that an outer panel has been compromised unless it has damaged a system or the impact site is leaking gas. Often, manual inspection of the station is required by performing spacewalks or by robotics to find potentially compromised areas.

An effective impact sensing system could be used to avert potential disasters of units in the space frontier from contact with space junk, and hypervelocity impacts of meteorites and micrometeoroids. A sensing system on the shields or exterior of a spacecraft may determine the shielding materials integrity during liftoff and flight through the earth's atmosphere. For example, if a piece of shielding had been displaced, a sensing system may determine where on the craft the shielding has been removed in the event it may be repaired once docked to the space station. This information may be communicated to the astronauts and the space flight control center to determine the extent of damage and to determine if the craft is a risk to astronaut's lives and/or critical equipment.

In the aircraft industry, active monitoring during all phases of an aircraft's life span will improve the safety margin of critical components. In the past, aircraft have had fuselage failures because fatigue cracks went undetected during the flight. If the skin of the aircraft is actively monitored, a pilot could be warned about developing problem(s) and mitigation actions could be taken. The information may also be fed into the aircraft's data recorder (i.e., "black box") providing greater detail on the aircraft's condition. This would lead to safer aircraft and extended aircraft lifespans.

In the commercial vehicle industry, a sensor system on key components of a vehicle may determine the extent of damage while a damage event, such as a collision is happening. This information may be used to deploy specific airbags to those areas of the vehicle being adversely affected or compromised.

In unmanned aerial vehicles (UAVs), battle field robots, autonomous systems, or any device requiring a circuit board, active monitoring may independently and quickly detect damage and automatically reroute signals, power, and command and control to other redundant systems without having to delay for error detection or other fault sensing techniques. This method may, for example, allow an autonomous robotic device to receive damage such as a bullet hole through a circuit board and automatically shut down the damaged section and reallocate lost functionality to other systems. Sensing systems which are capable of being adapted to design specifications of a microelectronic system may be utilized to improve the survivability of such microelectronic systems. For example, a sensing system which is light weight and easily mounted to an item of interest may provide continuous monitoring and enable a capacity for dynamically reconfiguring a circuit board for internal physical damage that may be caused by events such as physical trauma, shock, vibration or heat.

Sensing systems may also be used to identify breached containers holding sensitive documents, information, or materials. Such sensing systems should be easily monitored such that mitigation actions may be taken in real time before information/material is unrecoverable. Improvements to existing sensing technology are needed to detect a breach of any type of container for commercial or military use, and relay that breach to a monitoring system.

According to an illustrative embodiment of the present disclosure, a system is provided to produce real-time information on a variety of damage events, including structural, perimeter, and/or armor integrity failure conditions of a monitored device or unit by means of a resistive/conductive sensor system. One illustrative embodiment of the present disclosure provides sensors to areas where impacts may occur from a ballistic means or other known or unknown sources. Exemplary ballistic strike detection methods and structures may be used to pinpoint a location of an impact site, provide an estimation of the ballistic object's relative velocity, and provide an estimation of the ballistic object's size.

According to an illustrative embodiment of the present disclosure, a detection system includes a first layer adapted to a damage event, the first layer adapted to conduct an electromagnetic signal and having a plurality of electromagnetic signal measuring portions oriented in a first orientation. At least one coupling point is in electrical communication with at least one of the signal measuring portions of the first layer and is adapted to receive an electromagnetic signal input. An electromagnetic signal generator is coupled to the at least one input coupling point to provide the electromagnetic signal input. At least one output coupling point is in electrical communication with at least one of the signal measuring portions of the first layer and is adapted to provide an electromagnetic signal output. An electromagnetic signal measuring device is coupled to the at least one output coupling point. A processing system is adapted to control the electromagnetic signal generator and the electromagnetic signal measuring device, wherein the processing system is adapted to determine data on the damage event based on changes between the electromagnetic signal input at the at least one input coupling point and the electromagnetic signal output at the at least one output coupling point. The damage event may be further determined from an electromagnetic signal change calculation which is based on a comparison between a first electromagnetic signal measuring portion and a second electromagnetic signal measuring portion. Illustratively, an output device is adapted to produce damage data comprising a at least one of a damage alert, damage location, damage size, damage orientation, time data, and damage event category.

According to a further illustrative embodiment of the present disclosure, a detection system includes a sensing device configured to be operably coupled to a structure of interest and to sense a damage event. The sensing device includes a first layer, and a plurality of measuring portions supported by the first layer, each of the measuring portions including an input coupling point and an output coupling point and adapted to conduct an electrical signal from the input coupling point to the output coupling point. A measurement system is in electrical communication with the measuring portions of the sensing device, the measurement system configured to provide electrical signal inputs to the input coupling points of the sensing device, and configured to measure electrical signal outputs at the output coupling points of the sensing device. A damage detection processing system is operably coupled to the measurement system, the processing system configured to determine data on the damage event based on changes between the electrical signal inputs at the input coupling points and the electrical signal outputs at the output coupling points, the data including a location of the damage event on the sensing device and a damage event origination axis directed to the point of origin of the damage event. A user interface is operably coupled to the damage detection processing system and is configured to provide a visual display of the damage data including a representation of a damage alert, the damage event location and the damage event origination axis.

According to another illustrative embodiment of the disclosure, a method of detecting a damage event associated with a structure of interest includes the steps of coupling a first layer to a structure of interest, the first layer including a plurality of measuring portions oriented in a first direction, providing input electrical signals to input coupling points of each of the measuring portions, and measuring output electrical signals from output coupling points of each of the measuring portions. The method further includes the step of determining data on a damage event based on changes between the electrical signal inputs at each of the input coupling points and the electrical signal outputs at each of the output coupling points.

According to a further illustrative embodiment of the disclosure, a vehicle damage detection system includes a plurality of sensing devices supported by a vehicle and defining a sensing perimeter. Each of the sensing devices includes a layer, and a plurality of measuring portions supported by the layer, each of the measuring portions including an input coupling point and an output coupling point and adapted to conduct an electrical signal from the input coupling point to the output coupling point. A measurement system is in electrical communication with the measuring portions of each of the sensing devices. The measurement system is configured to provide electrical signal inputs to the input coupling points of each of the sensing devices, and is configured to measure electrical signal outputs at the output coupling points of each of the sensing devices. A plurality of couplers secure the plurality of sensing devices to an exterior of the vehicle. A damage detection processing system is operably coupled to the measurement system, and is configured to determine data on a damage event from the sensing devices based on changes between the electrical signal inputs at the input coupling points and the electrical signal outputs at the output coupling points, the data including a location of the damage event on the sensing device and a damage event origination axis directed to the point of origin of the damage event.

According to another illustrative embodiment of the present disclosure, a method of manufacturing a vehicle damage detection system includes the steps of preparing an outer surface of a vehicle to facilitate coupling thereto, applying a first electrically isolating material to the prepared surface of the vehicle, applying a first electrically conductive layer on the electrically isolative material, installing a plurality of electrical interconnects on the first electrically conductive layer, coupling the plurality of electrical interconnects to a measurement system, and applying an overcoat layer to the conductive layer and electrical interconnects.

According to yet another illustrative embodiment of the present disclosure, an event detection system includes an impact sensing device including a layer, and a plurality of measuring portions supported by the layer, each of the measuring portions including an input coupling point and an output coupling point and adapted to conduct an electrical signal from the input coupling point to the output coupling point. A measurement system is in electrical communication with the measuring portions of the impact sensing device. The measurement system is configured to provide electrical signal inputs to the input coupling points of the sensing device, and is configured to measure electrical signal outputs at the output coupling points of the sensing device. An acoustic detection system includes a plurality of microphones configured to detect soundwaves generated by an event. The acoustic detection system is configured to process time offsets from the soundwaves at the plurality of microphones for determining the direction of the source of the event. A processor is operably coupled to the measurement system and the acoustic detection system for determining a damage event origination axis directed to the point of origin of the event. The damage event origination axis is determined by the processor based on changes between the electrical signal inputs at the input coupling points and the electrical signal outputs at the output coupling points of the impact sensing device, and time offsets from the soundwaves at the plurality of microphones of the acoustic detection system. Further illustratively, an imaging system including at least one camera configured to detect weapon fire flash events may be operably coupled to the processor.

According to a further illustrative embodiment of the present disclosure, a method of detecting a damage event associated with a structure of interest includes the steps of providing a sensing device including a plurality of measuring portions, providing input electrical signals to input coupling points of each of the measuring portions, measuring output electrical signals from output coupling points of each of the measuring portions, and determining data on a damage event based on changes between the electrical signal inputs at each of the input coupling points and the electrical signal outputs at each of the output coupling points. The method further includes the steps of detecting soundwaves generated by the source of the damage event, detecting flash events from the source of the damage event, determining a damage event origination axis based on changes between the electrical signal inputs at the input coupling points and the electrical signal outputs at the output coupling points of the impact sensing device, and correlating the damage event origination axis with time offsets from the soundwaves at the plurality of microphones of the acoustic detection system, and the flash events from the imaging system.

According to a further illustrative embodiment of the present disclosure, an impact detection system includes a sensing device configured to be operably coupled to a structure of interest and to sense impacts. The sensing device includes a layer, and a plurality of measuring portions supported by the layer, each of the measuring portions including an input coupling point and an output coupling point and adapted to conduct an electrical signal from the input coupling point to the output coupling point. A measurement system is in electrical communication with the measuring portions of the sensing device. The measurement system is configured to provide electrical signal inputs to the input coupling points of the sensing device, and is configured to measure electrical signal outputs at the output coupling points of the sensing device. A damage detection processing system is operably coupled to the measurement system. The processing system is configured to determine data on a damage event from the sensed impact based on changes between the electrical signal inputs at the input coupling points and the electrical signal outputs at the output coupling points, the data including a location of the damage event on the sensing device and an damage event origination axis directed to the point of origin of the ballistic impact. A user interface is operably coupled to the damage detection processing system, the user interface including a plurality of visual indicators, the visual indicators including a plurality of light sources arranged in vertically spaced rows, each of the vertically spaced rows including a plurality of horizontally spaced light sources. Further illustratively, a targeting device is operably coupled to the measurement system. The targeting device may include a slewing mechanism configured to adjust elevation and azimuth of a targeting member for alignment with the origination axis.

According to a further illustrative embodiment of the present disclosure, a method of detecting a damage event associated with a structure of interest includes the steps of providing a sensing device including a plurality of measuring portions, providing input electrical signals to input coupling points of each of the measuring portions, measuring output electrical signals from output coupling points of each of the measuring portions, and determining data on a damage event based on changes between the electrical signal inputs at each of the input coupling points and the electrical signal outputs at each of the output coupling points. The method further includes the step of adjusting a targeting device in response to the data on the damage event.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which:

FIG. 3 is an exemplary exploded view of a multi-axis sensing device having layered structures that, when assembled, form a sensor system which permits impact detection and determination of a path of an impact object;

FIG. 4A is a diagrammatic side view of an illustrative layered sensing device showing a vector of a projectile impacting the sensing device;

FIG. 4B is a diagrammatic top view of the illustrative layered sensing device of FIG. 4A;

FIG. 5 is an exemplary plan view of a single-axis sensing device having a single layer with multiple sensing structures applied to a base surface;

FIGS. 6A and 6B are exemplary plan views of alternative embodiments of single-axis sensing devices, each having a single layer with multiple sensing structures for redundant sensing applied to a base surface;

FIG. 10 is an exemplary plan view of an alternative embodiment sensing device having with conductive layer and a series of electrical contacts on each side of the conductive layer;

FIG. 11 is an exemplary plan view of an alternative embodiment sensing device having a conductive layer with a gradient of resistance or electromagnetic properties across the layer and a series of electrical contacts on opposing sides of the conductive layer;

DETAILED DESCRIPTION OF THE DRAWINGS

The embodiments of the disclosure described herein are not intended to be exhaustive or to limit the disclosure to precise forms disclosed. Rather, the embodiments selected for description have been chosen to enable one skilled in the art to practice the disclosure.

An illustrative system in accordance with the present disclosure provides real-time information on a variety of damage events, including structural, perimeter, and/or armor integrity/failure conditions of a monitored device or unit by means of a electromagnetic (e.g., electrically resistive/conductive) sensor system. Damage events may include any event or activity that may affect structural integrity or cause failure. More particularly, it should be noted that damage events as described herein may be caused by a variety of sources including, but not limited to, impacts (e.g., ballistics, collisions, etc.), tamper or breaching activities (e.g., drilling, sawing, cutting, etc.), and structural/environmental induced damage (e.g., stress, fatigue, corrosion, etc.).

An exemplary embodiment of the disclosure includes sensing devices supported by areas of a structure of interest where impacts may occur from known or unknown sources, including from ballistic means. An exemplary impact detection and remediation system and method described herein may be used to pinpoint the location of an impact event, estimate the ballistic object's relative velocity, and estimate the ballistic object's size.

Figure 1:
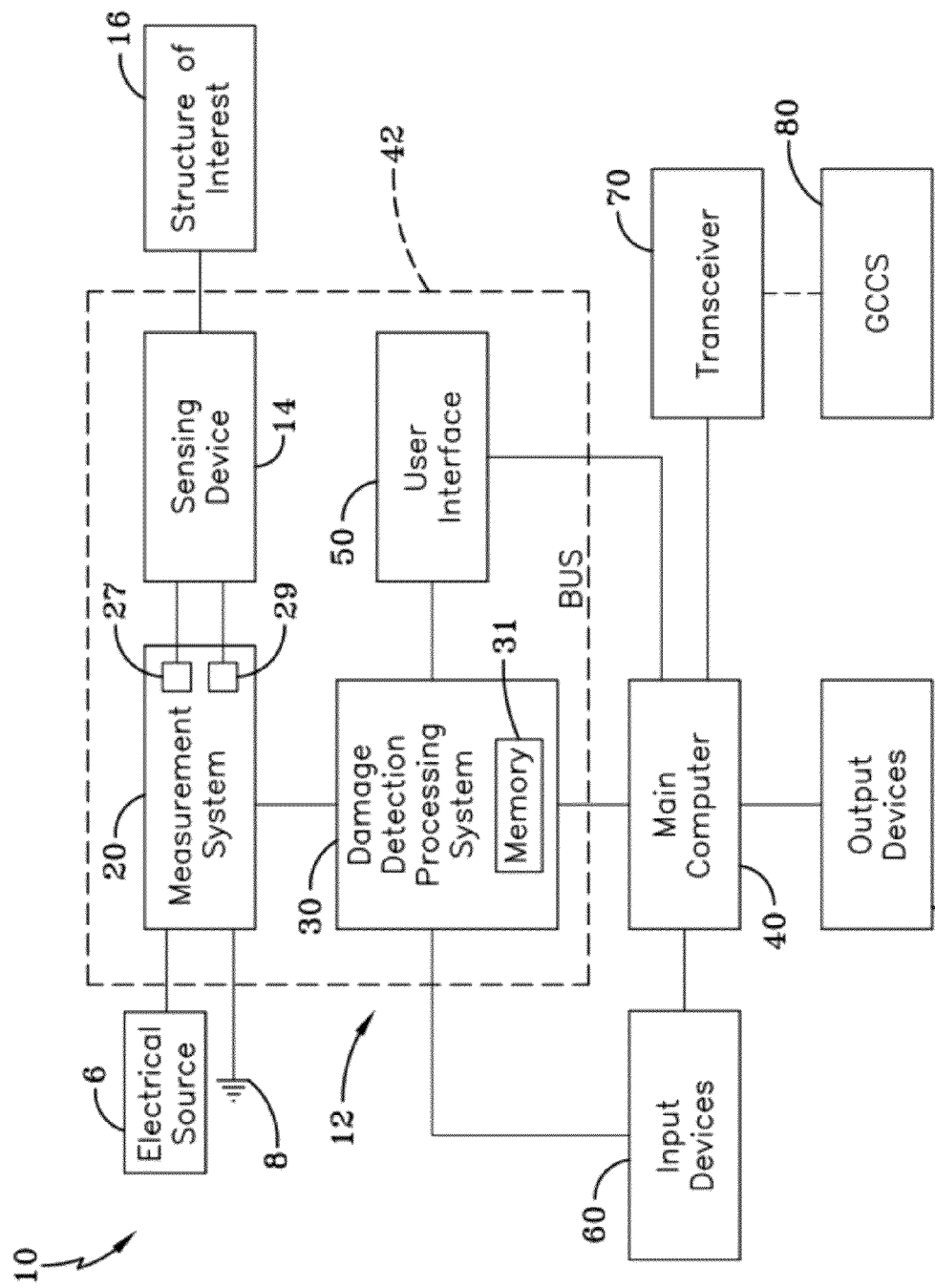
FIG. 1 is a block diagram of an illustrative damage detection and remediation system of the present disclosure, showing various representative input and output connections thereto.
Figure 2:
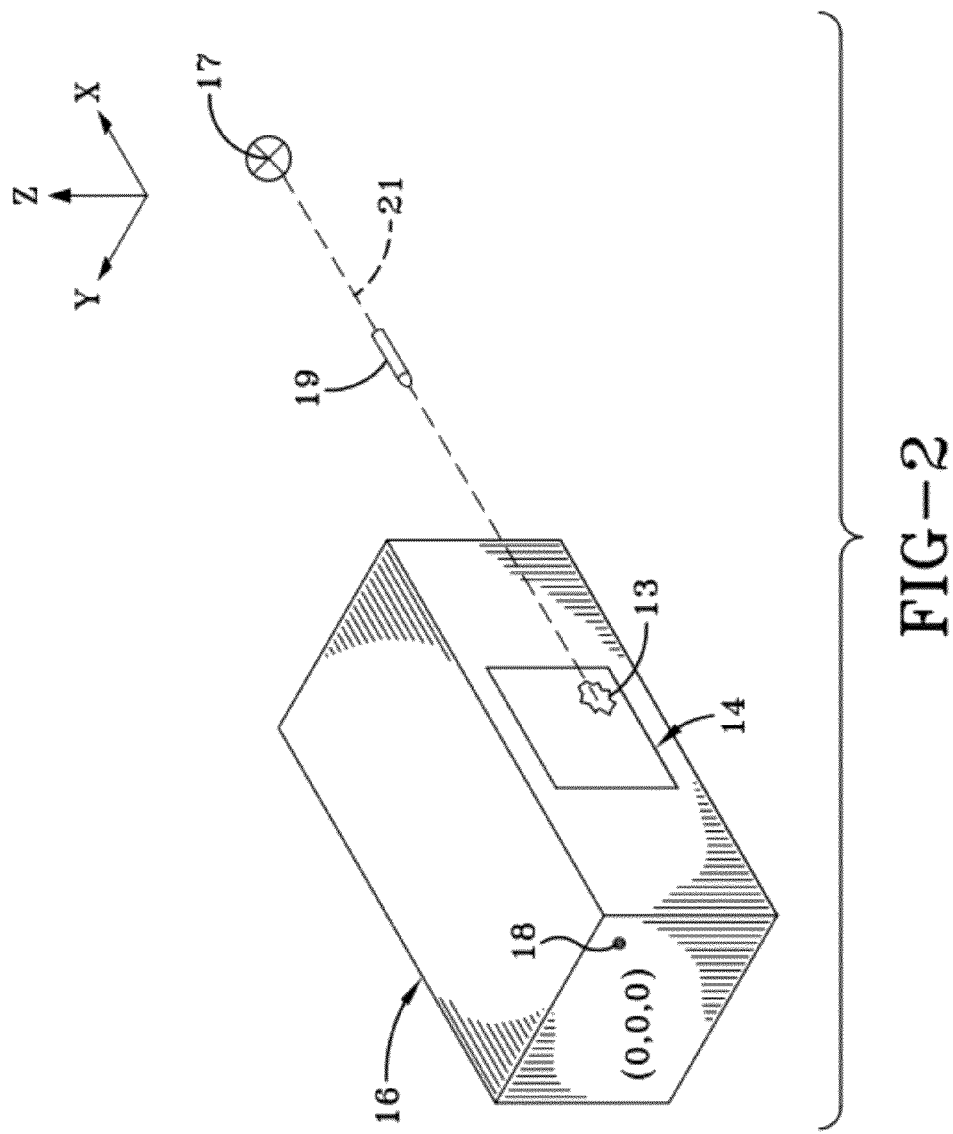
FIG. 2 is a diagrammatic view of an illustrative sensing device coupled to a structure of interest for determining a point of origin of an object impacting the sensing device.

With reference initially to FIGS. 1 and 2, a damage detection and remediation system 10 according to an illustrative embodiment of the present disclosure includes a sensor data acquisition and processing system 12 having a sensing structure or device 14 operably coupled to a monitored unit or structure of interest 16. As further detailed herein, the structure of interest 16 may include personal protective equipment, armor, vehicles, microelectronics, spacecraft, aircraft, or any other structure, device or unit where impact or damage detection is desired. The system 12 is configured to determine damage condition information, including the location of a damage or impact event 13 on the structure of interest 16 relative to a coordinate system origin 18 (0, 0, 0 on an x, y, z coordinate system). The system 10 may also be configured to determine the initiation or origin point 17 of an impact object or ballistic 19 and hence, an axis of origin (origination axis) 21 extending from the origin point 17 to the damage event 13. As further detailed herein, the system 10 may also characterize the impact object, for example, by determining the size of the damage event 13 and depth of penetration of the damage event 13.

The sensing device 14 is in electrical communication with a measurement system 20 which, in turn, is in electrical communication with a damage detection processing system 30. As further detailed herein, a main computer or processor 40 may be operably coupled to the data acquisition and processing system 12 for processing information from the damage detection processing system 30. An electrical bus 42 (FIG. 1) may interconnect a plurality of different data acquisition and processing systems 12 to each other and the main computer 40.

A user interface (UI) 50 may be in electrical communication with the damage detection processing system 30 and/or the main computer 40. The user interface 50 may form part of each data acquisition and processing system 12 or may be a separate component operably coupled to a plurality of systems 12. Additional input devices 60, such as image and/or acoustic sensing systems, as further detailed herein, may also provide input signals to the damage detection processing system 30 and/or main computer 40. A transceiver 70 may be operably coupled with the main computer 40 and provide wireless communication with external communication systems, such as a global control and command system (GCCS) 72. As further detailed herein, output devices 90 are illustratively in communication with the main computer 40 and may receive processed data (e.g., impact event location, ballistics' relative velocity and size, point of origin, etc.) and provide a desired response thereto.

Note that in connection with the following description, some drawings have dashed lines detailing elements of a structure which are not shown due to a cut-away or detailing a portion of a multi-layered design underneath a structure, such as in FIGS. 5, 6A, 6B, 6C, 8, 10, and 11. These dashed figure sections indicate the structure that would be present had the cut-away not been made in the drawing in question. These dashed structures are not present in the layer which has been exposed by the cut-away depiction in the drawing.

Referring now to FIG. 3, an exemplary sensing structure or device 14 in accordance with the disclosure is provided having multiple sensor layer assemblies 15a, 15b, 15c, each having a nonconductive substrate or layer 3, electrically conductive wires or traces 5 applied to the non-conductive layers 3, electrical contacts 7 adapted to be coupled to a first or output connection of measurement system 20, illustratively an electrical source 6 (hereinafter first electrical contacts 7), and electrical contacts 9 adapted to be coupled to a second or input connection of measurement system 20, illustratively a ground 8 (hereinafter second electrical contacts 9). Moreover, the first and second electrical contacts 7 and 9 are configured to electrically couple with any appropriate measuring device 20 such that the device 20 measures electrical characteristics therebetween (e.g., impedance, voltage, resistance, etc.).

Illustratively, the first electrical contacts 7 and the second electrical contacts 9 are coupled to opposing ends or termination points of each of the conductive wires or traces 5 for conducting electromagnetic (e.g., electrical) signals through traces 5 from first contacts 7 to respective second contacts 9. The FIG. 3 embodiment sensing device 14 shows a number of the wires or traces 5 evenly spaced apart, each running in parallel across the front face of each of the non-conductive layers 3. As further detailed herein, spacing between adjacent traces 5 defines system resolution by determining the number of impact data points.

The wires or traces 5 are illustratively read or monitored by the measurement system 20 checking each respective conductive path for an open, resistive change, or by transmitting an electromagnetic (e.g., electrical) signal pulse down the conductive path and measuring the time it takes to return or bounce back.

In one illustrative embodiment, the measurement system 20 includes an electromagnetic, illustratively electrical, signal generator 27 operably coupled to the electrical source 6 for providing a signal input to each of the first electrical contacts 7. The measurement system 20 also includes an electromagnetic, illustratively electrical, signal measuring device 29 operably coupled to the ground 8 for measuring signal outputs from each of the second electrical contacts 9.

In an illustrative embodiment, the measurement system 20 may comprise a time domain reflectometer (TDR) which is known for characterizing and locating faults in metal wires or cables. Illustratively, the TDR includes signal generator 27 in the form of an electrical pulse generator coupled to first electrical contacts 7 for transmitting a short time rise signal pulse along the traces 5. Assuming that each trace 5 is of uniform impedance and properly terminated, the entire transmitted pulse will be absorbed at second contacts 9 and no signal will be reflected back to the TDR. However, impedance discontinuities will cause some of the signal pulse from the signal generator 27 to be sent back towards the TDR. More particularly, increases in impedance will create a reflection that reinforces the original pulse signal, while decreases in impedance will cause a reflection that opposes the original pulse signal. The resulting reflected pulse signal is measured by signal measuring device 29 of the TDR, illustratively an oscilloscope that plots the reflected pulse signal as a function of time. Since the speed of signal transmission is relatively constant for conductive traces 5, the reflected pulse signal may be interpreted as a function of length to the damage 13.

As the different layer assemblies 15a, 15b, 15c (corresponding respectively to X, Y & U planes, where U represents a plane that is at an angle to X & Y planes) are penetrated by a ballistic object, the conductive wires or traces 5 at a damaged portion are cut or degraded, thereby identifying a location relative to a structure of interest. This damaged portion of the layers 15a, 15b, 15c also provides information on the size (i.e. surface area) and the depth of the damage.

With further reference to FIG. 3, an illustrative first sensor layer assembly 15a for a first sensor detection axis (e.g., "x axis") is provided with a number of electrically conductive wires or traces 5 running across the non-conductive layer 3 and spaced apart from each other in a perpendicular direction (e.g., "y axis"). Each of the conductive wires or traces 5 is illustratively embedded in the non-conductive layer 3. A decrease in spacing between adjacent conductive wires or traces 5 improves a given exemplary sensing structure's ability to sense size and impact location of an impact event (i.e., resolution) by providing a greater number of impact data points to the measurement system 20.

Embodiments of the sensing device 14 disclosure may be manufactured with a variety of materials. For example, the non-conductive layer 3 may be made from epoxy, thermoplastic, thermal set plastic, ceramic, paper, silicon, polymers, or other electrically non-conductive material suitable to having electrically conductive pathways coupled to the non-electrically conductive material. An electrically non-conductive material may also be applied using a spray or painting apparatus which applies the non-electrically conductive material onto a structure of interest then have the electrically conductive pathways applied onto a layer of the non-electrically conductive material. In one illustrative embodiment, the non-conductive layer 3 may be formed of an electrically isolative material, such as MYLAR®, fiberglass, KAPTON®. The conductive traces 5 may be formed of an electrically conductive material, such as copper or aluminum, which may be applied using conventional circuit trace processes, such as direct depositing, vapor depositing, etching, painting, flame spraying, laminating, or gluing the conductive material onto the isolative substrate or layer 3.

A second sensor layer assembly 15b for a second sensor detection axis (e.g., "y axis") is provided in the illustrative embodiment. The second sensor layer assembly 15b is similar to the first sensor layer assembly 15a except that the wires or traces 5 of the second sensor layer assembly 15b are oriented in a different direction than the wires or traces 5 in the first layer assembly 15a (e.g., angularly offset within a common plane). In this example, the wires or traces 5 in the second sensor layer assembly 15b are oriented to run approximately perpendicular to the wires or traces 5 in the first sensor layer assembly 15a.

A third sensor layer assembly 15c for a third sensor detection axis (e.g., "u axis") is provided in the illustrative embodiment. The third sensor layer assembly 15c is similar to the first and second sensor layer assemblies 15a, 15b, except that the wires or traces 5 that are of the third sensor layer assembly 15c are oriented in a different orientation than the first or second sensor layer assemblies 15a, 15b (e.g., angularly offset within a common plane). In this example, the wires or traces 5 of the third sensor layer assembly 15c are oriented at an approximate 45 degree angle relative to the wires or traces 5 in the first and second sensor layer assemblies 15a, 15b.

Referring further to FIG. 3, a rear face of the second sensor layer assembly 15b is coupled to a front face of the third sensor layer assembly 15c, illustratively through an adhesive. Similarly, a rear face of the first sensor layer assembly 15a is coupled to a front face of the second sensor layer assembly 15b, illustratively through an adhesive. In certain illustrative embodiments, the layer assemblies 15a, 15b, 15c may be coupled together through other conventional means, such as fasteners, heat staking, or lamination.

The embodiment sensing device 14 of FIG. 3 operates by coupling the electrical source 6 to the first electrical contacts 7, and ground 8 to the second electrical contacts 9. When a damage or impact event occurs (e.g., a ballistic object impact), resistance changes between the first electrical contacts 7 and the second electrical contacts 9 when the wires or traces 5 are either severed or deformed at the damaged portion.

Measurement system 20 is illustratively coupled to the electrical source 6 and ground 8 which determines changes in electrical properties of the wires or traces 5. More particularly, the signal generator 27 of the measurement system 20 electrically couples the first electrical contacts 7 to the electrical source 6, and the signal measuring device 29 of the measurement system 20 electrically couples the second electrical contacts 9 to ground 8. The measurement system 20 will then send measurements to impact or damage detection processing system 30 which then determines damage data (e.g., the location, size, time, and/or category of a damage event 13 on the structure of interest 16 to which the sensing device 14 has been coupled).

The impact detection processing system 30 may use the relative position of each impact event location associated with each sensor layer assembly 15a, 15b, 15c to determine the impact location 13 for the object 19 which created the impact event. This information may then be used to identify the point of origin 17 for the object 19 associated with the impact event. The point of origin 17 information may then be used to take further actions such as orienting output devices 90 (e.g., further sensors or equipment) on the axis of origin 21 to further respond, if necessary, to potential additional impact events.

The damage data from the processing system 30 may then be provided to a user interface 50. More particularly, the user interface 50 may include an output device to produce damage data including a visual representation of a damage alert, damage event 13 location, and a damage event origination axis 21. In certain illustrative embodiments, the user interface 50 may include a graphical display for plotting the damage event 13 location on a diagram or map associated with the structure of interest 16. In certain illustrative embodiments, the user interface 50 may provide an audible event warning and/or a tactile event warning indicating the location of the damage event 13. The user interface 50 may also include a communication device, such as a wireless transceiver, that transmits a damage event notification signal depicting an orientation of the damage event 13.

The axis of origin 21 information may also be used to determine or assess damage which could have been caused by the impact or penetration associated with the damage event 13 and impact object 19. An embodiment of the system 10 may also be used to characterize the impact object 19 and potentially the source 17 of the impact object 19 based on axis of origin 21, size of damage 13 detected by the sensor layer assemblies 15a, 15b, 15c, and depth of penetration of damage 13 within the sensor layer assemblies 15a, 15b, 15c, to further characterize threat or other information associated with the impact object 19 or event. The user interface 50, such as a display monitor or other graphical user interface device, then permits a user to view and interpret the plot of damage, axis of origin 21 for the impact object 19, and potential area of interest for a point of origin 17 of the impact object 19, and take appropriate action.

FIGS. 4A and 4B are diagrammatic views showing how a vector 22 for a projectile 19 impacting sensing device 14 may be determined by system 10. A table of damage profile data associated with impact damage 13a, 13b, 13c (FIG. 4A) at layer assemblies 15a, 15b, 15c from specific sources may be created by system 12 and stored in memory 31. The processing system 30 may correlate the detected damage 13 with expected damage characteristics from known sources stored in the damage profile data table. For example, damage profile data may represent known damage profiles from common sources, such as AK47 rounds, anti-tank rounds, and IED damage patterns so the system will not produce false vector information from anything except rifle or gun rounds. IED or armor piercing blast damage would likely cause so much damage that the damage pattern could not be interpolated to produce an accurate vector 22 calculation for the point of origin 17. Additional illustrative stored damage profiles may be from a small arms (e.g., 3 mm to 8 mm projectiles) category, an explosively formed penetrator category, a high energy ballistic impact category (e.g., micro meteoroids or space debris), a structural fatigue category, a heat event category, and a large caliber (e.g., .50 or larger caliber) projectile category.

Referring to FIG. 5, a further illustrative embodiment sensing device 24 is shown as including a sensor layer assembly 26 having elongated loops of wires or traces 25, 27, 29, 31, 33, and 35 running across a nonconductive layer 23 with first (e.g., source) and second (e.g., ground) electrical contacts 7 and 9, respectively, coupled to each respective end of the elongated loops of wire or traces 25, 27, 29, 31, 33, and 35. In the illustrative embodiment, the first and second electrical contacts 7 and 9 are formed on one side of the sensor layer assembly 21 and are coupled to opposing ends of each elongated loop 25, 27, 29, 31, 33, and 35. The non-conductive layer or substrate 23 is illustratively formed of an electrically isolative material (e.g., MYLAR®, fiberglass, KAPTON®, or epoxy), while the loops of wires or traces 25, 27, 29, 31, 33, and 35 are illustratively formed of an electrically conductive material (e.g., copper or aluminum). A base material or substrate 22 is illustratively placed underneath the non-conductive layer 23. However, it should be noted that the base material 22 could also be the structure of interest 16 that is being monitored for an impact event which the non-conductive layer 23 is placed upon versus another layer of material. The elongated loops of wire or traces 25, 27, 29, 31, 33, and 35 are placed such that they are parallel with each other and are approximately evenly spaced apart across the non-conductive material 23.

The loops of wire or traces 25, 27, 29, 31, 33, and 35 are illustratively read or monitored by the measurement system 20 checking each respective conductive path for an open, resistive change, or by transmitting an electromagnetic (e.g., electrical) signal pulse down the conductive path and measuring the time it takes to return or bounce back. In certain illustrative embodiments, the sensing device 24 of FIG. 5 may be operably coupled to a time domain reflectometer (TDR) for operation similar to sensing device 14 of FIG. 3, but for having the electrical contacts 7 and 9 all located along one side of the non-conductive layer 23.

Referring to FIGS. 6A and 6B, further illustrative sensing devices 41 and 71 are shown. Sensing device 41 is shown as including two nested sensor loops 47, 69, while sensing device 71 is shown as including six nested sensor loops 77, 78, 80, 82, 84, 86. The nested and multiple sensor loops provide enhanced capability to impact position detection system 10 by increasing its ability to detect smaller damage areas and impact objects 19 impinging on a structure of interest 16 as well as location of impact 13. The operation of the first embodiment sensing device 41 and second embodiment sensing device 71 in FIGS. 6A and 6B, respectively, are both substantially identical with the exception than the second embodiment sensing device 71 of FIG. 6B has a greater ability to sense smaller objects within a smaller area than the first embodiment sensing device 41 of FIG. 6A.

The illustrative sensing device 41 shown in FIG. 6A includes a non-conductive material layer or substrate 45 placed on a base material or substrate 43, with a first sensor loop 47 and a second sensor loop 69 formed on the electrically isolating or non-conductive layer 45. Again, the base material 43 may be the structure of interest 16 that is being monitored for an impact event and upon which the non-conductive layer 45 is directly placed versus an intermediate layer of material. Both the first sensor loop 47 and the second sensor loop 69 are illustratively formed of an electrically conductive material (e.g., copper or aluminum).

The first sensor loop 47 of sensing device 41 illustratively has a first end on an upper right hand side of the non-conductive material 45. The first sensor loop 47 extends in a continuous elongated serpentine path, or manner similar to an elongated sine wave form, with lengths of each lateral loop segment being longer than a vertical length forming bend segments from top to bottom of the non-conductive material 45 with even spacing. However, it should be noted that the sensing device 41 may include any sensor loop or structure form which adequately covers a structure of interest 16 to provide a sensing capacity distributed over the structure of interest 16 as desired. The sensor loop 47 in sensing device 41 has a terminating or second end on a lower right hand side of the non-conductive material 45 of FIG. 6A. A first end electrical contact 49 is formed in electrical contact with the first end of the sensor loop 47 at the upper right hand corner of the sensing device 41. A second end electrical contact 55 is formed in electrical contact with the second end of the sensor loop 47 proximate the lower right hand corner of the sensing device 41. A number of intermediate electrical contacts 67, 63, and 61, are coupled to bend points intermediate end contacts 49 and 55 in the elongated serpentine path of sensor loop 47 in sensing device 41.

The second sensor loop 69 of the sensing device 41 of FIG. 6A is illustratively formed similar to the first sensor loop 47 in an elongated serpentine form which is nested to follow the contours or shape of the first sensor loop 47. The sensor loop 69 has an initiating or first end on a lower left hand portion of the sensing device 41, and has a terminating or second end at an upper left section of the sensing device 41 of FIG. 6A. A first end electrical contact 59 is formed in electrical contact with the first end of the sensor loop 69 at the lower left hand section of the sensing device 41. A second end electrical contact 65 is formed in electrical contact with the second end of the sensor loop 69 proximate the lower right hand corner of the sensing device 41. A number of intermediate electrical contacts 57, 53, and 51 are coupled to bend points intermediate end contacts 59 and 65 in the elongated serpentine path of the second sensor loop 69 in sensing device 41.

The sensor loops 47 and 69 are illustratively read or monitored by the measurement system 20 checking each respective conductive path for an open, resistive change, or by transmitting a pulse down the conductive path and measuring the time it takes to return or bounce back. As further detailed herein, any suitable measurement device may be coupled across first end electrical contacts 49 and 59 and electrical contacts 55, 67, 63, 61, and 65, 57, 53, 51 to measure electrical attributes of the sensor loops 47 and 69, respectively. In certain illustrative embodiments, the measurement system may comprise a time domain reflectometer (TDR). As such, the sensing device 41 of FIG. 6A may operate in a similar manner as the sensing device 24 of FIG. 5.

The illustrative sensing device 71 of FIG. 6B shows a non-conductive layer or substrate 75 placed on a base material or substrate 73 with first, second, and third sensor loops 77, 78, 80 formed in elongated U shaped forms having an initiating or first end at a right hand side and a terminating or second end on the right hand side with the bend being on an opposing side, such that the opening defined by the U shape of each loop 77, 78, 80 is formed on the right hand side. The non-conductive layer 75 is illustratively formed of an electrically isolative material (e.g., MYLAR®, fiberglass, KAPTON®, or epoxy), while the loops 77, 78, 80 are illustratively formed of an electrically conductive material (e.g., copper or aluminum). The first, second, and third sensor loops 77, 78, 80 are illustratively evenly spaced apart, with the first sensor loop 77 being formed in an upper section, the second sensor loop 78 being formed in a center section, and the third sensor loop 80 being formed in a lower section of the sensing device 71. First electrical contacts 79, 83, 87 are respectively formed in electrical contact with a beginning or an upper side of the U-shaped first, second, and third sensor loops 77, 78, 80 on the right side of the sensing device 71 in FIG. 6B. Second electrical contacts 81, 85, 89 are formed in electrical contact with a respective opposing end of the first, second, and third sensor loops 77, 78, 80 having first electrical contacts 79, 83, 87, and are likewise positioned on the right side of the sensing device 71 in FIG. 6B.

FIG. 6B shows the illustrative sensing device 71 as including fourth, fifth and, sixth sensor loops 86, 84, 82 formed in elongated U shaped forms starting from a left hand side and ending on the left hand side. The bend in the U shaped form of each loop 86, 84, 82 is formed on an opposing side from the end points of each U shaped loop 86, 84, 82 such that the opening of the U shape is formed on the left hand side of the sensing device 71 in FIG. 6B. The fourth, fifth, and sixth sensor loops 86, 84, 82 are formed evenly spaced apart, with the fourth sensor loop 86 being formed in an upper section, the fifth sensor loop 84 being formed in a center section, and the sixth sensor loop 82 being formed in a lower section of the sensing device 71. First electrical contacts 103, 99, 95 are respectively formed in electrical contact with a beginning point or an upper side of the U-shaped fourth, fifth, and sixth third sensor loops 86, 84, 82 on the left hand side of the sensing device 71 in FIG. 6B. Second electrical contacts 101, 97, 91 are formed in electrical contact with a respective opposing end of the fourth, fifth, and sixth sensor loops 86, 84, 82 having first electrical contacts 103, 99, 95.

The first, second, and third sensor loops 77, 78, 80 of the illustrative sensing device 71 of FIG. 6B are offset and nested within the fourth, fifth, and sixth sensor loops 86, 84, 82. End points of sensor loops which terminate within a nested portion of another sensor loop (e.g., first sensor loop 77 which terminates inside of fourth sensor loop 86, and sixth sensor loop 82 which terminates inside third sensor loop 80), are electrically coupled with a corresponding electrical contact using a buried trace within the non-conductive material 73 (e.g., first electrical contact 81 is electrically coupled with the end of the first sensor loop 77, and second electrical contact 95 is electrically coupled with the end of the sixth sensor loop 82).

The sensor loops 77, 78, 80 are illustratively read or monitored by the measurement system 20 checking each respective conductive path for an open, resistive change, or by transmitting a pulse down the conductive path and measuring the time it takes to return or bounce back. Again, in certain illustrative embodiments, the measurement system 20 may comprise a time domain reflectometer (TDR). As such, the sensing device 71 of FIG. 6B may operate in a similar manner as the sensing device 41 of FIG. 6A.

More particularly, the method of operation and processing systems for use with the illustrative sensing devices 41 and 71 of FIGS. 6A and 6B may be similar to those detailed above in connection with sensing device 14 of FIG. 3. The single-axis device embodiments of FIGS. 6A and 6B may be primarily focused on identifying a location of a damage event 13, versus the multi-axis embodiment of FIG. 3 which is also configured to determine a point of origin 17 of an object 19 causing a damage event 13 (FIG. 2). However, it should be appreciated that layering sensing devices 41 and 71 (alone or with additional devices) would create a multi-axis sensing device having sensing features similar to sensing device 14 of FIG. 3.

Figure 6C:
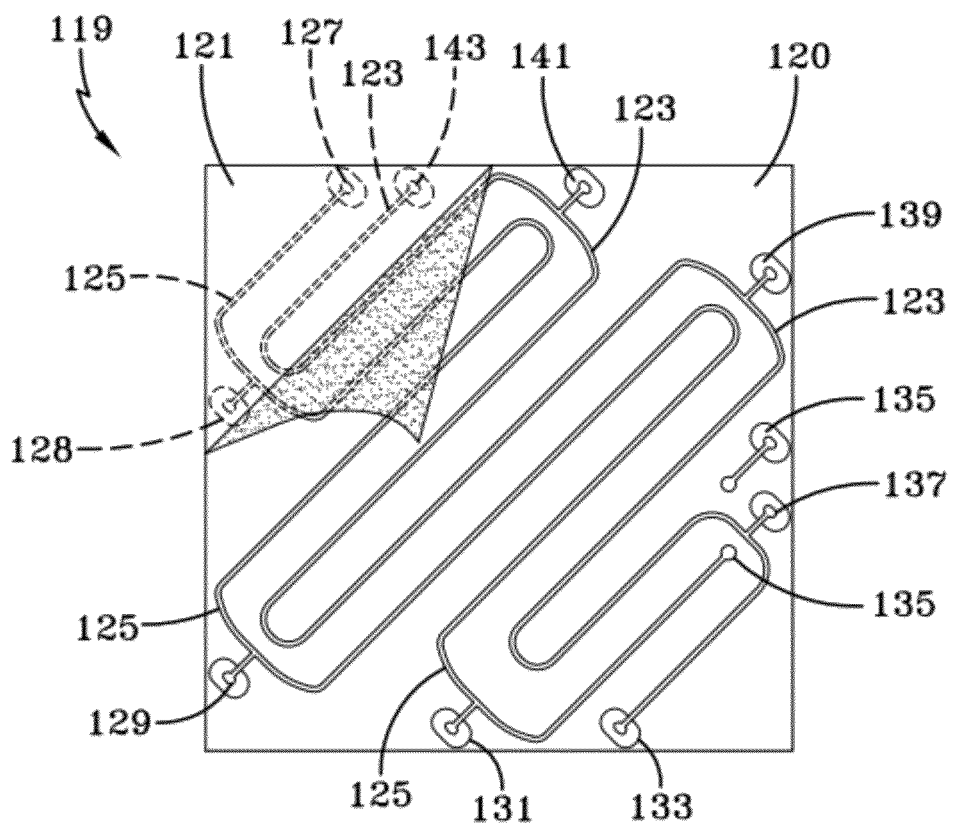
FIG. 6C is an exemplary plan view of an alternative embodiment single-axis sensing device with multiple electrical detection loops oriented at an angle with respect to a designated plane which provides an ability to detect smaller objects more precisely.

FIG. 6C shows an exemplary alternative impact sensing device 119 of a single axis sensing structure with multiple electrical detection loops 123, 125 formed onto a non-conductive material substrate or layer 120 oriented with an angle with respect to a designated plane. The impact sensing device 119 provides an ability to detect smaller impact objects more precisely. In particular, the sensing device 119 of FIG. 6C shows first and second sensor loops 123, 125 which are coupled with the non-conductive material 120. Again, the non-conductive layer 120 is illustratively formed of an electrically isolative material (e.g., MYLAR®, fiberglass, KAPTON®, or epoxy), while the loops 123, 125 are illustratively formed of an electrically conductive material (e.g., copper or aluminum). The first and second sensor loops 123, 125 are formed in an elongated serpentine path with lateral segments and bend segments which couple to the lateral segments in a U shaped form. The lateral segments are longer than the bend segments. The lateral segments are formed with an orientation which is approximately 45 degrees from a designated plane of interest such a ground plane which is parallel to a terrestrial horizon. The first and second sensor loops 123, 125 are offset and nested within each other's loops 125, 123, with the first sensor loop 123 starting at a top left hand section of the impact sensing device 119 in FIG. 6C and ending in a lower right hand section of the impact sensing device 119.

With further reference to FIG. 6C, a first end electrical contact 143 is illustratively formed on the upper left hand portion of the impact sensing device 119 and is coupled to the first sensor loop 123. First end electrical contact 127 is formed on the upper left hand portion of the impact sensing device 119 and is coupled to the second sensor loop 125. Intermediate electrical contacts 141, 139, 137 are formed on each bend segment of the first sensor loop 123, and a second end electrical contact 133 is formed at an end section of the first sensor loop 123 on the lower right hand section of the sensing device 119. Intermediate electrical contacts 128, 129, 131 are formed on each bend segment of the second sensor loop 125 and an second end electrical contact 135 is formed at an end section of the second sensor loop 125 on the lower right hand section of the sensing device 119. In this embodiment, each electrical contact 141, 139, 137, 133, 128, 129, 131, 135 is separate from respective first end electrical contacts 143, 127 to permit measuring of discrete electrical attributes therebetween, such as resistance values.

Again, in certain illustrative embodiments, the measurement system 20 coupled to sensing device 119 may comprise a time domain reflectometer (TDR). As such, the sensing device 119 of FIG. 6C may operate in a similar manner as the sensing device 41 of FIG. 6A. Further, sensing devices 41, 71, and 119 (alone or with additional devices) may be layered to create a multi-axis sensing device having sensing features similar to sensing device 14 of FIG. 3. For example, sensing device 41 may form a top layer, sensing device 71 may form an intermediate layer, and sensing device 119 may form a bottom layer.

Figure 7:
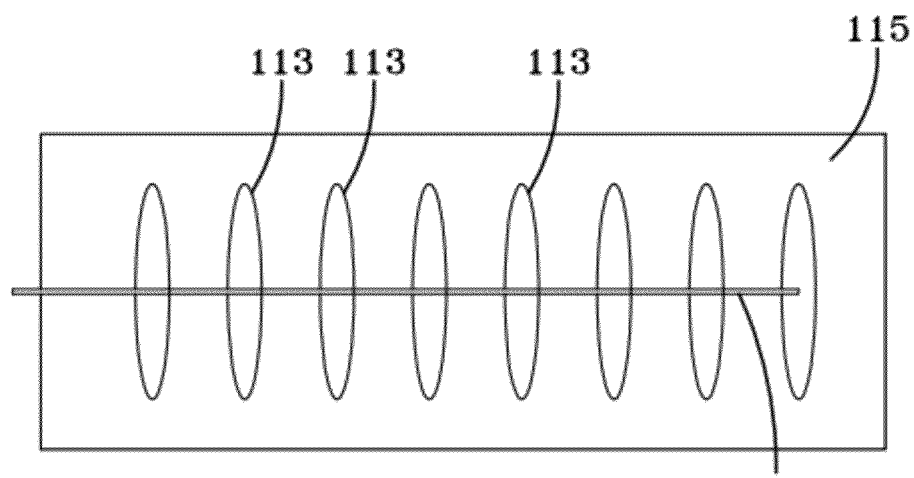
FIG. 7 is an exemplary diagrammatic view of an electromagnetic radiating structure with a electromagnetic wave propagating through free space from the radiating structure.

FIG. 7 shows an exemplary model of a further sensing system, illustratively including an electromagnetic radiating structure 111 (e.g., an antenna) with an electromagnetic wave 113 propagating through free space from the radiating structure 111. The electromagnetic wave 113 in this example is perpendicular to a ground plane 115. An impact object 19 traversing the electromagnetic wave 113 will distort the electromagnetic wave 113 as it passes through the electromagnetic wave 113 field. This distortion may be detected and plotted using damage detection processing system 30 which permits detection of an impact object 19 prior to impact. This system may be adapted to detect background radiation or electromagnetic sources and then emit a field which is out of phase with the background radiation or electromagnetic sources which then cancels one or more background radiation or electromagnetic signals so as not to avoid emitting an interference field or create an undesirable detectable signal.

In certain illustrative embodiments, radiating structure 111 may comprise a proximity sensor similar to a Theremin. The Theremin may include a plurality of spaced apart antennas supported by a base plate defining a ground plane. An illustrative Theremin is the Model No. 302 Theremin available from Harrison Instruments of Silver Spring, Md. Illustratively, at least three antennas are provided in order to facilitate triangulation of an object (such as a ballistic) positioned in proximity to the Theremin. While the antennas may be of any suitable shape and size, in certain illustrative embodiments the antennas are configured to extend parallel to, and are illustratively recessed within, the base plate defining the ground plane. In operation, the plurality of antennas are configure to detect the presence, location, and velocity of an object by detecting changes in the electromagnetic waves detected by the antennas within the medium (e.g., air) above the ground plane. The antennas are also configured to detect changes in the electromagnetic waves as a result of damage events (e.g., holes, recesses, etc.) within the external surface of the base plate.

Figure 8:
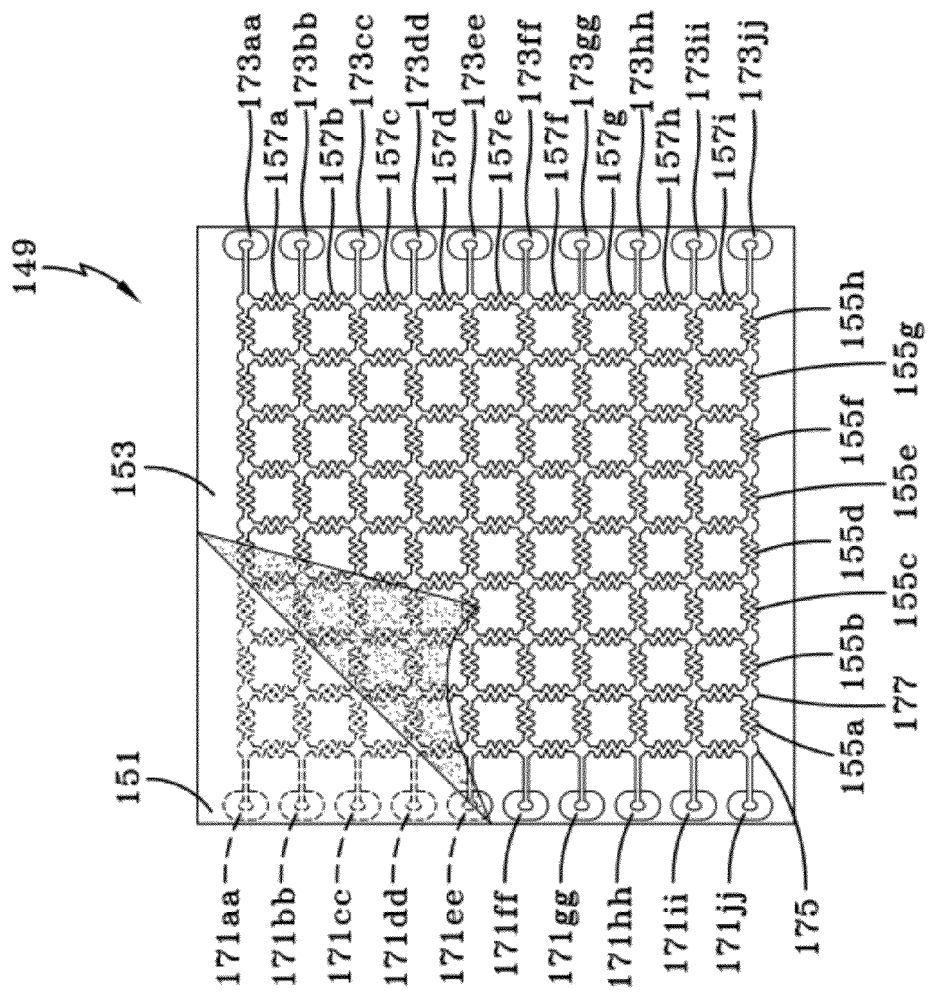
FIG. 8 is an exemplary plan view embodiment of an alternative sensing device with an array of embedded resistance elements having different electrical resistance values across the array contained in one or more planes of the sensing device prior to an impact.

FIG. 8 shows an exemplary embodiment of an alternative single or multiple-axis sensing device 149 with an array of embedded resistance elements having different electrical resistance values across the array contained in one or more planes of the sensing device 149 prior to an impact. The sensing device 149 may be coupled, adhered, or attached to a base material layer or substrate 151 or directly to the structure of interest 16. The impact sensing device 149 illustratively includes a non-conductive material 153 and an array of embedded resistive elements 155 and 157 formed into rows and columns, respectively (e.g., each row includes resistive elements 155$a$-155$h$, and each column includes resistive elements 157$a$-157$i$). The sensing device 149 resistive elements 155, 157 are coupled at interconnects or nodes at each intersection of the respective rows and columns. In the illustrative embodiment of FIG. 8, there are nine columns and ten rows of resistive elements 155,157, and each individual resistive element has two interconnects for electrical conductivity. For example, a first resistive element 155$a$ in row ten, column one has two interconnects on either side of the first resistive element (e.g., 175, 177).

With further reference to FIG. 8, measurement system 20 is electrically coupled to first and second electrical contacts 171 and 173, respectively, to measure electrical attributes (e.g., impedance, voltage, resistance) therebetween. In one illustrative embodiment, power signals are applied via measurement system 20 to first electrical contacts 17, and measurements are taken by measurement system 20 at second electrical contacts 173 to determine electrical attributes of the impact sensor array 149. Note that a single drawing element number has been assigned to each first electrical contact 171 and each second electrical contact 173, followed by a pair of letters. The signal path between each opposing first electrical contact 171 and second electrical contact 173 is illustratively measured independently from every other signal path. Moreover, each pair of contacts 171, 173 defining a signal path are identified by reference numbers 171, 173 followed by the same letter (i.e., 171$aa$, 173$aa$ defines a first signal path, 171$bb$, 173$bb$ defines a second signal path, etc.). The use of the single drawing reference number for all contacts of the same category (e.g., electrical source contacts 171) should not be used to infer a limitation on the design, structure, or processes used in this embodiment of the disclosure with reference to the contacts themselves. In other words, measurements in this embodiment may be taken between respective first and second electrical contacts 171, 173 in the same row, as well as in different rows.

A different measurement of electrical attributes (e.g., impedance, voltage, resistance) may be taken for each row by means of measuring via measurement system 20 each first and second electrical contacts 171, 173 in a row independently of the other rows in the exemplary impact sensor array 149. In particular, measurements are taken which permit determination of impact events based on measuring electrical attributes from each path between first electrical contacts 171 and second electrical contacts 173. In certain illustrative embodiments, measurements may be taken by the measurement system 20 between each first electrical contact 171 and every second electrical contact 173. For example, measurements may be taken between first electrical contact 171$aa$ and each of the second electrical contacts 173$aa$-173$jj$, between first electrical contact 171$bb$ and each of the second electrical contacts 173$aa$-173$jj$, and so forth, concluding with measurements taken between first electrical contact 171$jj$ and each of the second electrical contacts 173$aa$-173$jj$.

As shown in FIG. 8, a series of resistors 155 is illustratively placed between nodes that are formed at the intersection of each column and row. For example, a series of resistors 155$a$, 155$b$, 155$c$, 155$d$, 155$e$, 155$f$, 155$g$, 155$h$, are coupled to each other serially with a first electrical contact 171$jj$ on one interconnect of the first resistor 155$a$ in row ten, and a second electrical contact 173$jj$ on one interconnect of the last resistor 155$h$ in row ten. Each resistor 155 may have a different resistance value between the first resistor 155$a$ and the last resistor 155$h$ in row ten. The values of each resistor 155 in each row in this embodiment are illustratively formed to individually and serially have a range from low to high, high to low, or a different resistance value. More particularly, each resistor 155 in a row in this embodiment may have a different resistance value than the other resistors 155 in the same row. For example, the first resistor 155$a$ in row ten may have a 50 ohm resistance, the second resistor 155$b$ in row ten may have a 45 ohm resistance, the third resistor 155$c$ in row ten may have a 40 ohm resistance, the fourth resistor 155$d$ in row ten may have a 35 ohm resistance, the fifth resistor 155$e$ in row ten may have a 30 ohm resistance, the sixth resistor 155$f$ in row ten may have a 25 ohm resistance, the seventh resistor 155$g$ in row ten may have a 20 ohm resistance, and the eighth resistor 155$h$ in row ten may have a 15 ohm resistor. Each row in this illustrative embodiment sensing device 149 may have a similar scheme of resistance or electrical attribute values, e.g., high to low, low to high, or different resistance. In this illustrative embodiment, resistors 157 which form the column links between nodes formed by the rows and columns are of the same resistance values. However, the individual column resistors 157 may also be selected to have different resistance values such as a progression of high to low resistance, low to high resistance, or different resistance values for two or more resistors 157 from column to column. An embodiment may also exist where both rows and columns both have different resistance values. The selection of a gradient change in resistance values in this embodiment contributes to provide a capability of determining position of impact in the impact sensing device 149.

Figure 9:
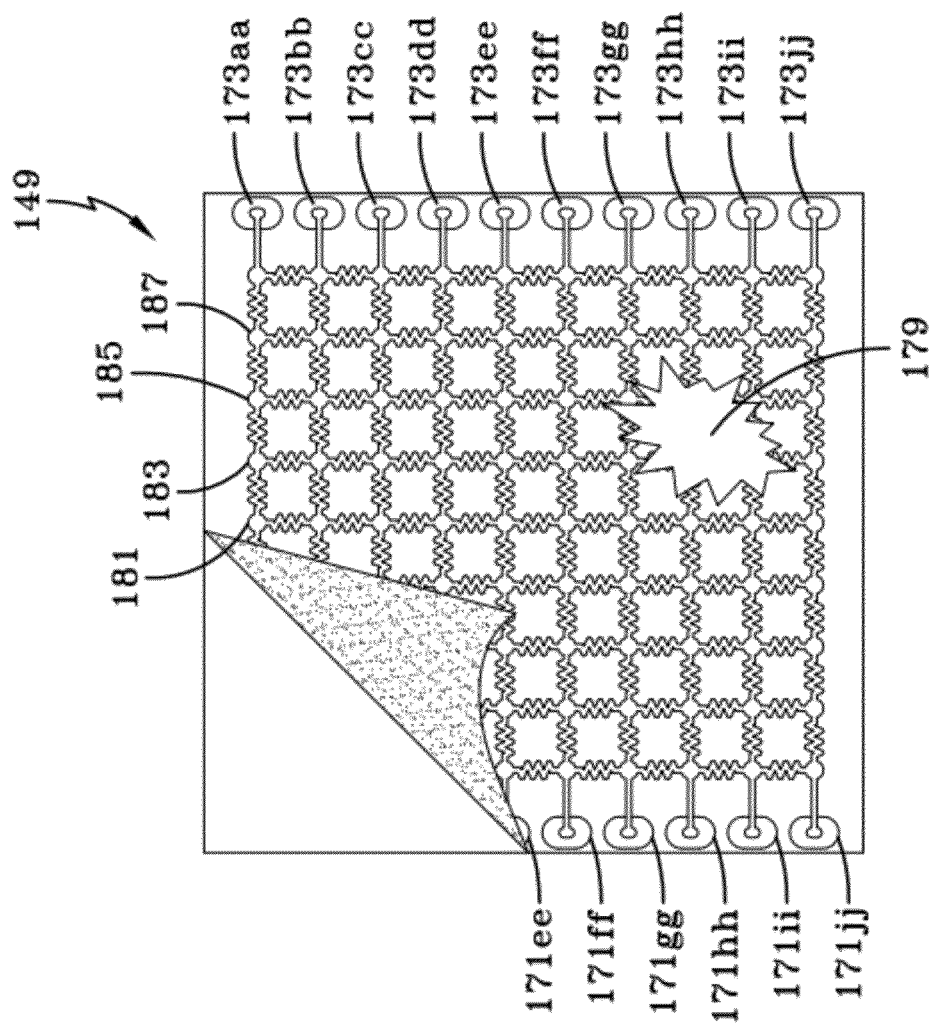
FIG. 9 is a plan view similar to FIG. 8, showing the sensing device during or after an impact.

Referring to FIG. 9, the sensing device of FIG. 8 is shown during or after an impact event. The illustrative sensing device of FIG. 8 is shown with ten rows (corresponding to first electrical contacts 171$aa$-171$jj$) and nine columns (including a fifth column 181, a sixth column 183, a seventh column 185, and an eighth column 187 as shown in FIG. 9). The enumeration of the rows (i.e., first, second, third), starts at a top row then progresses downward, and the column enumeration (i.e., first, second, third), starts at an upper left most column and progresses to the right. An impact area or damage zone 179 is formed after an impact event in the impact sensing device 149. Resistors 155, 157 are damaged or disconnected from the impact sensor array 149 as a result of the exemplary impact event. As a result, a resistance path changes between first electrical contacts 171gg, 171hh, 171ii and second electrical contacts 173gg, 173hh, 173ii due to the impact area or damage zone. In other words, an electrical path changes between these respective contacts 171gg and 173gg, 171hh and 173hh, 171ii and 173ii. For example, an electrical path between first electrical contact 171hh and second electrical contact 173hh will now substantially take an electrical path of resistors 155 in the eighth row 171hh to the resistors 157g, 157f between eighth and sixth rows 171hh and 171ff in the fifth column, then travel along row 171ff to a node at row 171ff and column eight 187, then to the resistor 157f, 157g between rows 171ff and 171hh to the node at the eighth row 171hh and column eight 187, then complete the path to second electrical contact 173hh through the eight row 171hh. The sensing device of FIGS. 8 and 9 operates by measuring resistance and then matching or determining which pathways are still active versus ones that are not which then determines the path of least resistance. This path of least resistance data may then be used to determine which sections of the impact sensing device 149 are still present and which ones that are not or are degraded, and thereby determine a plot or position of impact event damage to the impact sensing device 149.

FIG. 10 shows an exemplary alternative embodiment of a multiple axis impact sensing structure or device 191 with a conductive layer 193. A first series of first electrical contacts 197a-197k, a second series of first electrical contacts 199a-199l, a first series of second electrical contacts 201a-201k, and a second series of second electrical contacts 203a-203l are electrically coupled to the conductive layer 193. The first series of first electrical contacts 197a-197k are illustratively applied to a left hand outer edge of the conductive layer 193. The second series of first electrical source contacts 199a-199l are illustratively applied to a top outer edge area of the conductive layer 193. The first series of second electrical contacts 201a-201k are illustratively applied to a right hand outer edge of the conductive layer 193. The second series of second electrical contacts 203a-203l are illustratively applied to a bottom outer edge of the conductive layer 193. The first and second series of first electrical contacts 197a-197k and 199a-199l, respectively, and the first and second series of second electrical contacts 201a-201k and 203a-203l, respectively, are evenly distributed along the above described outer edges of the conductive layer 193 and are in electrical contact with the conductive layer 193. The conductive layer 193 may be manufactured from a variety of materials which are homogenous with respect to electrical conductivity (e.g., copper, aluminum, or carbon). More particularly, the conductive layer 193 may be formed of any material having suitable electrical attributes for the sensing methodology detailed herein. The illustrative embodiment impact sensing device 191 operates by sensing electrical attributes (e.g., impedance, resistivity, conductivity) between first electrical contacts 197a-197k and 199a-199l and second electrical contacts 201a-201k and 203a-203l.

Measurements from the sensing of electrical attributes by the sensing device 191 may be processed by processing system 12, which then determines position and size of impact events 13 by a variety of calculations. More particularly, electrical attributes are illustratively processed by the measurement system 20 which then communicates with the damage detection processing system 30. The processing system 30 may include a triangulation processor, which based on paths of least resistance or a look up table stored in memory 31, associates position and size of damage with electrical attribute data such as resistance or conductance sensed between at least one set of first electrical contacts 197, 199 and any of the second electrical contacts 201, 203.

In an exemplary embodiment of sensing device 191, the measurement system 20 may serially or in parallel measure an electrical attribute (e.g., resistance), between first electrical contacts 197a-197k and opposing second electrical contacts 201a-201k, as well as between first electrical contacts 199a-199l and opposing second electrical contacts 203a-203l to determine electrical attributes sensed in the electrically conductive layer 193 between the respective contacts 197, 199, 201, 203. The damage detection processing system 30 determines an electrical attribute data value between one or more pairs of selected first and second electrical contacts 197 and 201, 199 and 203. At least two of the electrical data values associated with two or more pairs of selected first and second electrical contacts 197 and 201, 199 and 203 may be used in a triangulation method by damage detection processing system 30 for identifying a damage area based on comparing a known electrical data value associated with a pre-damage state of the electrically conductive layer 193 to a post-damage event state of the electrically conductive layer 193. Additional electrical data values associated with additional pairs of selected first and second electrical contacts 197 and 201, 199 and 203 may be further used by the processing system 30 in the triangulation processor to determine additional size information associated with a damage area 13.

In an illustrative example, a first electrical data value associated with a post-damage state of the electrically conductive layer 193 may be sensed by the measurement system 20, for example through a read-out bus coupled to first electrical contact 197c and second electrical contact 201i. A second electrical data value associated with a post-damage state of the electrically conductive layer 193 may be sensed by the measurement system 20, for example through a read-out bus coupled to first electrical contact 199j and second electrical contact 203c. If a damage event 13 has occurred between these above reference contacts (197c, 201i and 199j, 203c in this example), then a higher resistance value will be detected in the electrically conductive layer 193 where the conductive layer 193 has been damaged or degraded between the sensed contact points (e.g., 197c, 201i and 199j, 203c). In this example, if the electrically conductive layer 193 has been damaged between, for example, first electrical contact 197c and second electrical contact 201i, then a resistance reading between these contacts (e.g., 197c, 201i and 199j, 203c) will show a higher resistance value than a baseline resistance value associated with an undamaged electrically conductive layer 193. Obtaining at least two electrical data values, where each electrical data value is associated with a linear path of least resistance between two opposing first and second electrical contacts 197, 199 and 201, 203 creates a coordinate point for determining position of a damage event 13 to the electrically conductive layer 193.

The coordinate point of the damage event 13 referenced above may be determined by the damage detection processing system 30 based on a comparison of the electrical attributes or data values sensed between any two given first and second electrical contacts 197, 199 and 201, 203, for example, by showing higher resistance thereby indicating damage as compared to a baseline resistance associated with no damage to the electrically conductive layer 193. Higher sensed resistance data between sensed first electrical contacts 197, 199 and second electrical contacts 201, 203 may be used by processing system 30 to create a virtual impact damage plot comprising intersecting virtual damage plot lines representing damage coordinates (i.e., two sets of intersecting first and second electrical contacts 197, 199 and 201, 203 showing higher resistance across the electrically conductive layer 193). The processing system 30 may then plot damage to the electrically conductive layer 193 using the above reference damage coordinates and output this damage position to the user interface 50 which may then be used to determine further responses or action by either a user, for example through user interface 50, or an output device 90, such as a machine which is operably coupled to the processing system 30.

FIG. 11 shows an exemplary alternative embodiment impact sensing structure or device 211 including an electrically conductive layer 213 having varying electrical or electromagnetic properties across the electrically conductive layer 213 sensed by means of a series of electrical contacts 215, 217 positioned along opposing sides. In one illustrative embodiment, the layer 213 has a gradient of resistance (e.g., high to low, or low to high from left side to right side of the layer 213). In other words, the layer 213 includes a gradient defined as a plane with a high material conductivity on one side, and a low material conductivity on an opposite side. Illustratively, the layer 213 may be formed of graphite, known to be a good resistive material.

The series of electrical contacts comprise first electrical contacts 215a-215k and second electrical contacts 217a-217k electrically coupled to the layer 213. Illustratively, the first electrical contacts 215a-215k are electrically coupled to a left outer edge of the electrically conductive layer 213, while the second electrical contacts 217a-217k are electrically coupled to a right outer edge of the electrically conductive layer 213. The second electrical contacts 217a-217k are illustratively arranged equidistant from each other along the right outer edge of the electrically conductive layer 213. The first electrical contacts 215a-215k are also illustratively arranged equidistant from each other along the left outer edge of the electrically conductive layer 213. The measurement system 20 senses electrical attributes such as resistance or conductance between any two first and second electrical contacts 215 and 217. The damage detection processing system 30 referenced above may determine position and size of an impact event 13 which damages or degrades the electrically conductive layer 213.

With further reference to the illustrative impact sensing device 211 of FIG. 11, a first virtual grid line 221a may be determined between first electrical contact 215a and second electrical contact 217k based on a first electrical data measurement which is different from a baseline measurement previously determined between these two contacts 215a and 217k. A second virtual grid line 221b may be determined between first electrical contact 215b and second electrical contact 217j based on a second electrical data measurement which senses an electrical attribute between these two contacts 215b and 217j which is different from a baseline measurement previously determined between these two contacts 215b and 217j. Subsequent virtual grid lines 221c-221k may be determined between each successive pair of contacts 215c-215k and 217i-217a.

In the FIG. 11 embodiment impact sensing structure 211, the different resistances measured across the electrically conductive layer 213 assist in correlating the size and location of the impact event damage or degradation in the electrically conductive layer 213. In other words, the virtual grid line 221 between any pair of first and second electrical contacts 215 and 217 will have a different value due to the change in resistance across the electrically conductive layer 213. In this embodiment, a lookup table stored in memory 31 may be used by damage detection processing system 30 to facilitate determination of position and size of impact event damage 13 in the electrically conductive layer 213.

Figure 12:
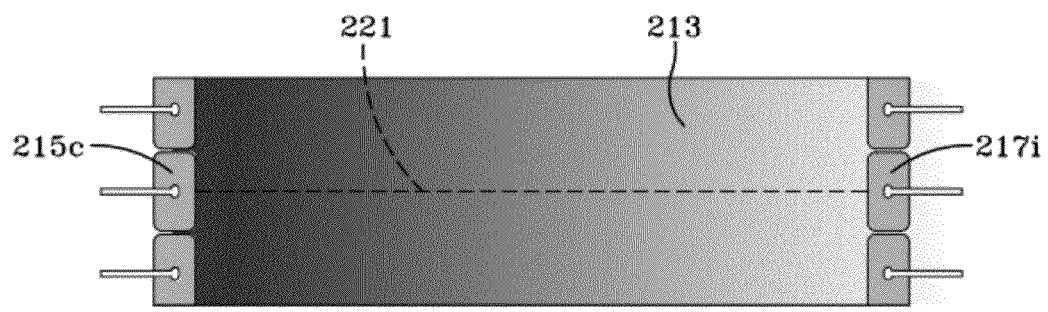
FIG. 12 is an exemplary detailed plan view of the sensing device of FIG. 11 showing a conductance layer shown before an impact.

FIG. 12 is a detailed view of exemplary impact sensing structure 211 of FIG. 11 showing a portion of the conductive layer 213 before an impact. A dashed line represents a virtual grid line 221 between first electrical contact 215c and second electrical contact 217i through the electrically conductive layer 213. An electrical data measurement is sensed by the measurement system 20 coupled to the first and second electrical contacts 215c and 217i. More particularly, the measurement system 20 senses an electrical attribute between these two electrical contacts 215c and 217i. In the FIG. 12 embodiment, there is no damage between these two electrical contacts 215c and 217i, therefore the sensed electrical data measurement is not different from a baseline measurement previously determined between these two electrical contacts 215c and 217i and stored in memory 31. As such, the processing system 12 determines no damage exists between first and second electrical contacts 215c and 217i.

Figure 13:
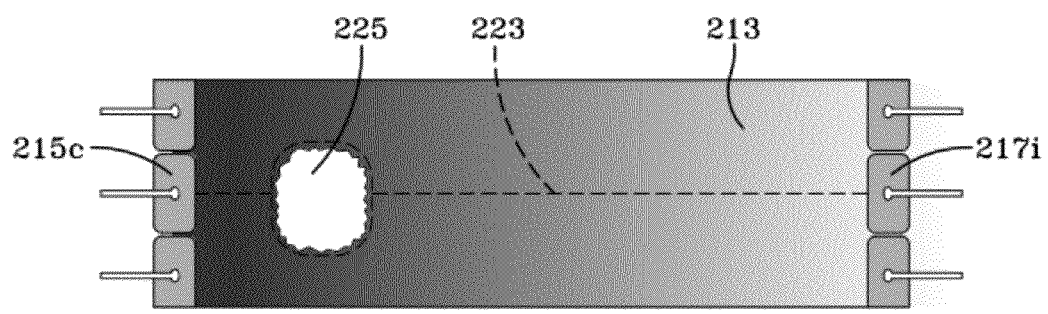
FIG. 13 is an exemplary detailed plan view of the sensing device of FIG. 11 showing a conductance layer shown during or after an impact.

FIG. 13 is a detailed view similar to FIG. 12 of exemplary impact sensing structure or device 211 having the conductive layer 213 after an impact event creating an impact damage area 225 in the electrically conductive layer 213. A dashed line represents a virtual grid line 223 between first electrical contact 215c and second electrical contact 217i around the impact damage area 225 in the electrically conductive layer 213. An electrical data measurement is sensed by the measurement system 20 coupled to the electrical contacts 215c and 217i. More particularly, the measurement system 20 senses an electrical attribute between these two electrical contacts 215c and 217i. In the FIG. 13 embodiment of sensing device 211, there is damage between these two electrical contacts 215c and 217i in the form of impact damage area 225. As such, the sensed electrical data measurement is different from a baseline measurement previously determined between these two electrical contacts 215c and 217i (FIG. 12) and the damage detection processing system 30 determines that damage exists between these two electrical contacts 215c and 217i. The measurement system 20 takes additional electrical data measurements between additional pairs of first electrical contacts 215 and second electrical contacts 217 in order to create additional virtual grid lines 233 which are associated with the impact damage area 225 and are used by processing system 30 to further refine position and size information associated with the impact damage area 225.

Embodiments of the sensing devices of the present disclosure may be affixed directly to the structure of interest 16 which is desired to be monitored for impact or tampering, be built into the structure of interest 16, or be formed into structures which may be selectively attachable and detachable from a structure of interest 16. An embodiment of the disclosure may be selectively attached or detached from a structure of interest 16 by means of couplers, such as a latching system, hooks, hook and loop fasteners (i.e., Velcro), latches, screws, adhesives, or other suitable fasteners.

FIGS. 14-18 shows steps associated with an exemplary method of manufacture for installing an exemplary impact sensing structure 211 as in FIG. 11 onto a portion of a structure of interest 16, such as a vehicle 231. While structure of interest 16 is shown in FIGS. 14-18 as a vehicle, and more particularly as a tank, it should be appreciated that that impact sensing structure 211 may be used on a wide variety of structures, including aircraft, ships, spacecraft, and containers.

Figure 14:
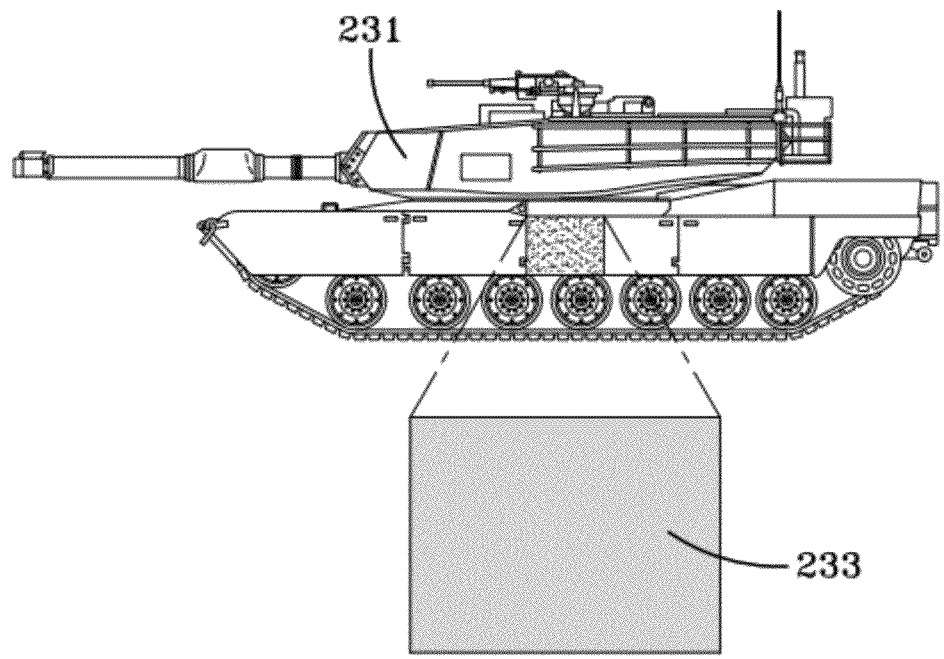
FIG. 14 is an exemplary side elevational view showing a first method of manufacture step for surface preparation needed to ensure a required adhesion of subsequent layers associated with installation of an exemplary sensing device such as shown in FIG. 11 installed onto a facing of an equipment item where detection is desired.

FIG. 14 shows an exemplary first method of manufacture step for preparing a surface 233 needed to ensure a required adhesion of subsequent layers associated with installation of an exemplary sensing structure 211 installed onto a facing or outer surface of the vehicle 231 where detection is desired. A surface preparation step of FIG. 14 may comprise processing which ensures adhesion or coupling with the exemplary sensing structure 211 which is to be installed in a later step. Such surface preparation may include sanding and/or attaching couplers or coupling structures, such as hook and loop fasteners (i.e., Velcro®) bolts, latches, or adhesives, to the structure of interest 231 where the coupling structures are adapted to releasably or non-releasably couple to the exemplary sensing structure 211 which is installed in a later step.

Figure 15:
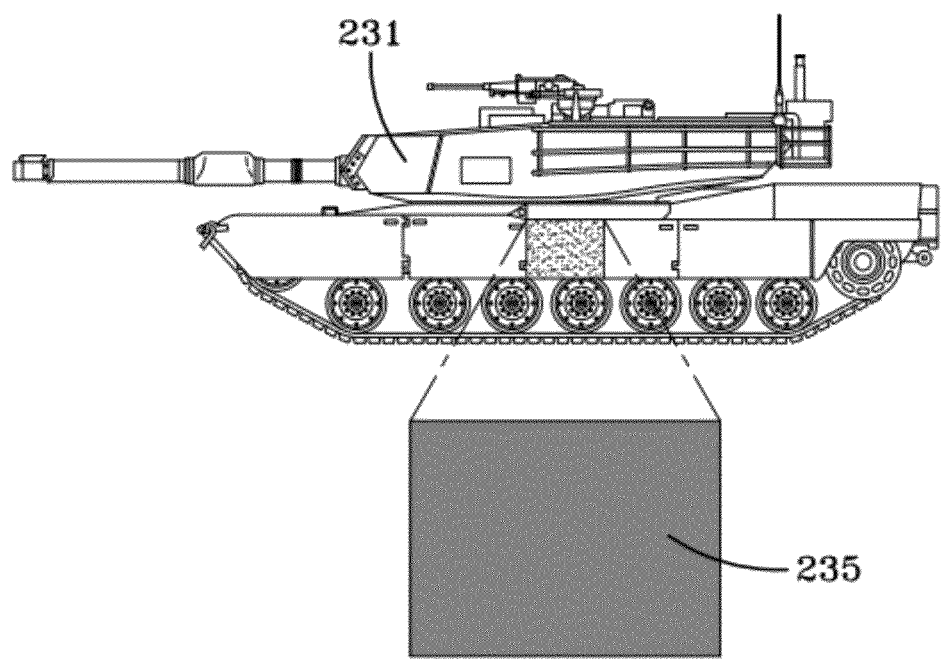
FIG. 15 is an exemplary side elevational view showing a second method of manufacture step for applying an electrically insulating material associated with installation of an exemplary sensing structure such as shown in FIG. 11 installed onto a facing of an equipment item where detection is desired.

FIG. 15 shows an exemplary second method of manufacture step for applying an electrically isolating (i.e., non-conductive) material 235 to define a non-conductive layer associated with a later installation of an exemplary sensing structure 211, such as that shown in FIG. 11, installed onto a facing of the equipment item 231 where detection is desired. Illustratively, this step comprises applying an electrically isolative base layer, for example a polymer paint, on the prepared surface 233. The electrically isolating material 235 may be applied using a spray or painting apparatus which applies the material 235 onto the prepared surface. The isolating material 235 may illustratively be made from epoxy, polymers, including thermoplastics and thermosets, ceramic, paper, silicon, or other electrically non-conductive material suitable to having electrically conductive pathways coupled to the non-electrically conductive material. In certain illustrative embodiments, the electrically isolating material 235 may comprise MYLAR®, fiberglass, or KAPTON®.

Figure 16:
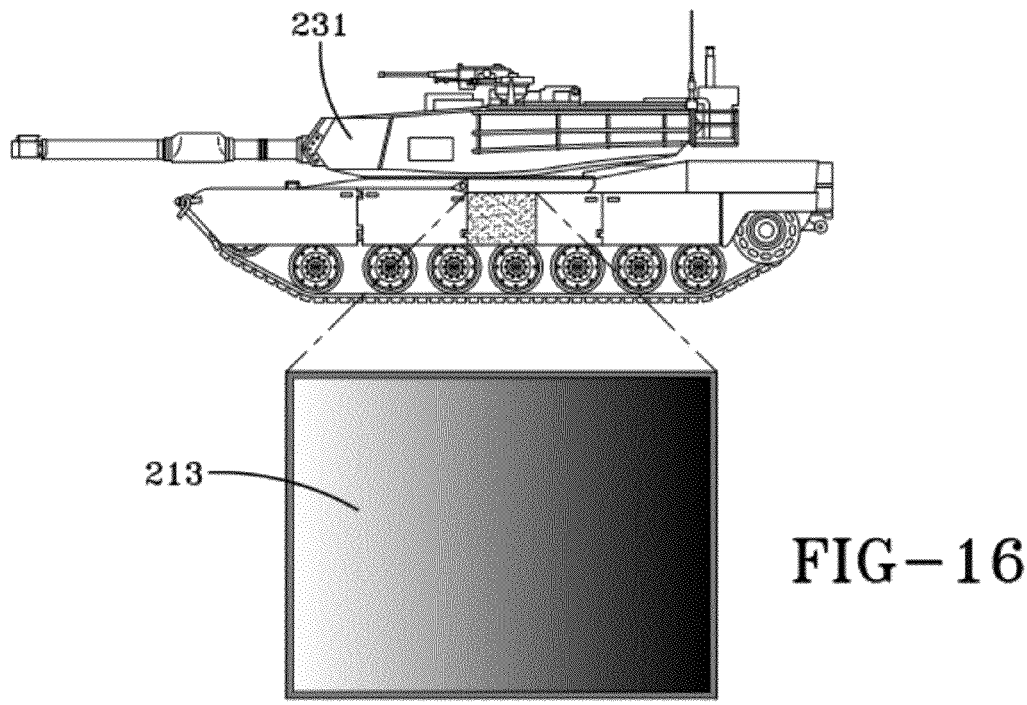
FIG. 16 is an exemplary side elevational view showing a third method of manufacture step for applying an exemplary conductance layer associated with a sensing structure such as shown in FIG. 11 installed onto a facing of an equipment item where detection is desired.

FIG. 16 shows an exemplary third method of manufacturing step for applying an exemplary conductive layer 213 associated with a sensing structure, such as shown in FIG. 11, installed onto a facing of the equipment item 231 where detection is desired. Illustratively, conductive layer 213 may be formed of graphite as it is known to be a good variable resistive material. The conductive layer 213 may be formed of any suitable electrically conductive material, such as copper or aluminum, which may be applied using conventional circuit trace processes, such as direct depositing, vapor depositing, etching, painting, flame spraying, laminating, or gluing the conductive material onto the electrically isolating material 235.

Figure 17:
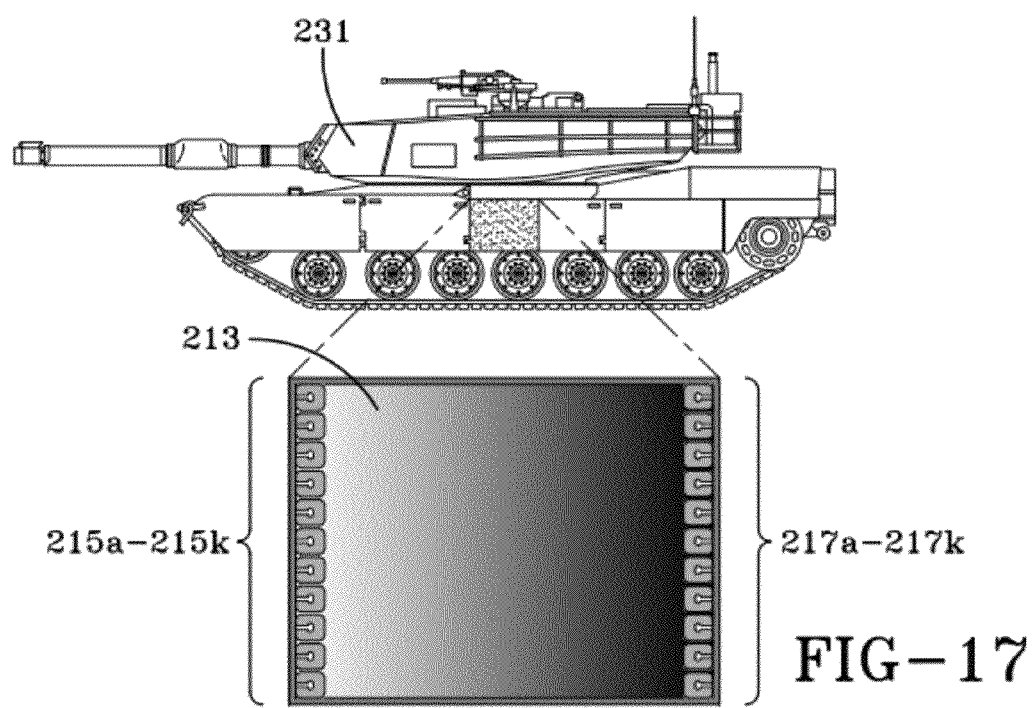
FIG. 17 is an exemplary side elevational view showing a fourth method of manufacture step for applying electrical interconnects to the conductance layer associated with a sensing structure such as shown in FIG. 11 installed onto a facing of an equipment item where detection is desired.

FIG. 17 shows an exemplary fourth method of manufacturing step for applying electrical interconnects, illustratively first and second electrical contacts 215a-215k and 217a-217k, to the electrically conductive layer 213 associated with sensing structure 211 installed onto a facing of an equipment item 231 where detection is desired. The electrical contacts 215a-215k and 217a-217k are illustratively electrically coupled to the layer 213 through conductive epoxy and electrically coupled to the measurement system 20 through inset copper or flexible copper circuit buses.

Figure 18:
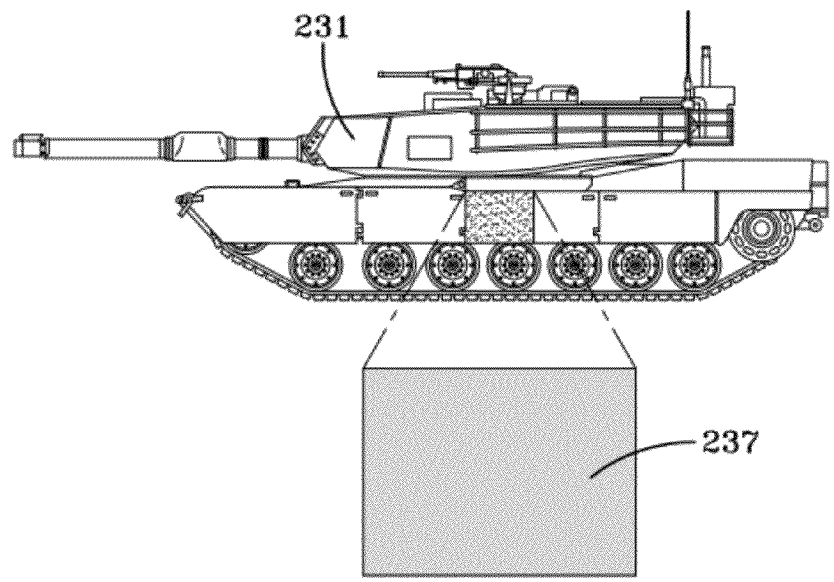
FIG. 18 is an exemplary side elevational view showing a fifth method of manufacture step for applying a layer which will provide protection and concealment of the structures previously provided associated with a sensing structure such as shown in FIG. 11 installed onto a facing of an equipment item where detection is desired.

FIG. 18 shows an exemplary fifth method of manufacturing step for applying an overcoat layer 237 which will provide protection and concealment of the structures previously provided in FIGS. 14-17 associated with a sensing structure, such as shown in FIG. 11, installed onto a facing of the vehicle 231 where detection is desired. Illustratively, the layer 237 is formed of an electrically isolative material for preventing the sensor layer from shorting out and for protecting the sensor layer from the environment. The layer 237 may comprise a polymer paint of a color matching the exterior surface of the vehicle 231 for concealment of the sensing device 211.

In further illustrative embodiment methods of manufacture, additional electrically isolative and conductive layers may be successively applied intermediate the electrically isolative layer 235 and the electrically conductive layer 213. Each grouping of electrically isolative and conductive layers 235 and 213 may define separate sensor layer assemblies 15a, 15b, 15c similar to the type detailed above in connection with FIG. 3.

Figure 19:
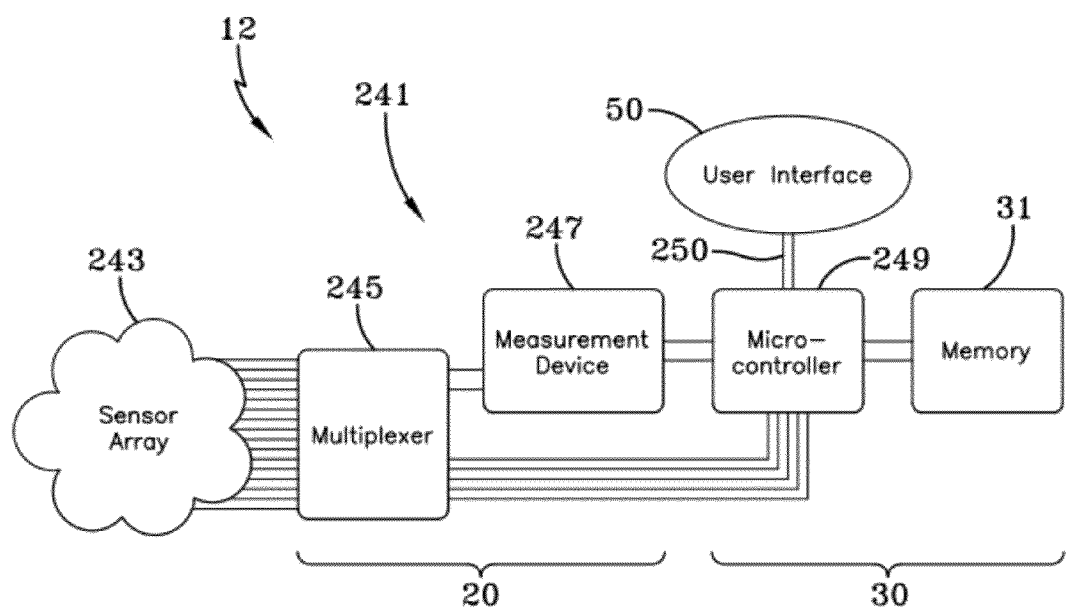
FIG. 19 is a detailed block diagram of a portion of the damage detection and remediation system of FIG. 1, showing an illustrative sensor data acquisition and processing system coupled to a sensing structure in accordance with an illustrative embodiment of the disclosure.
Figure 20:
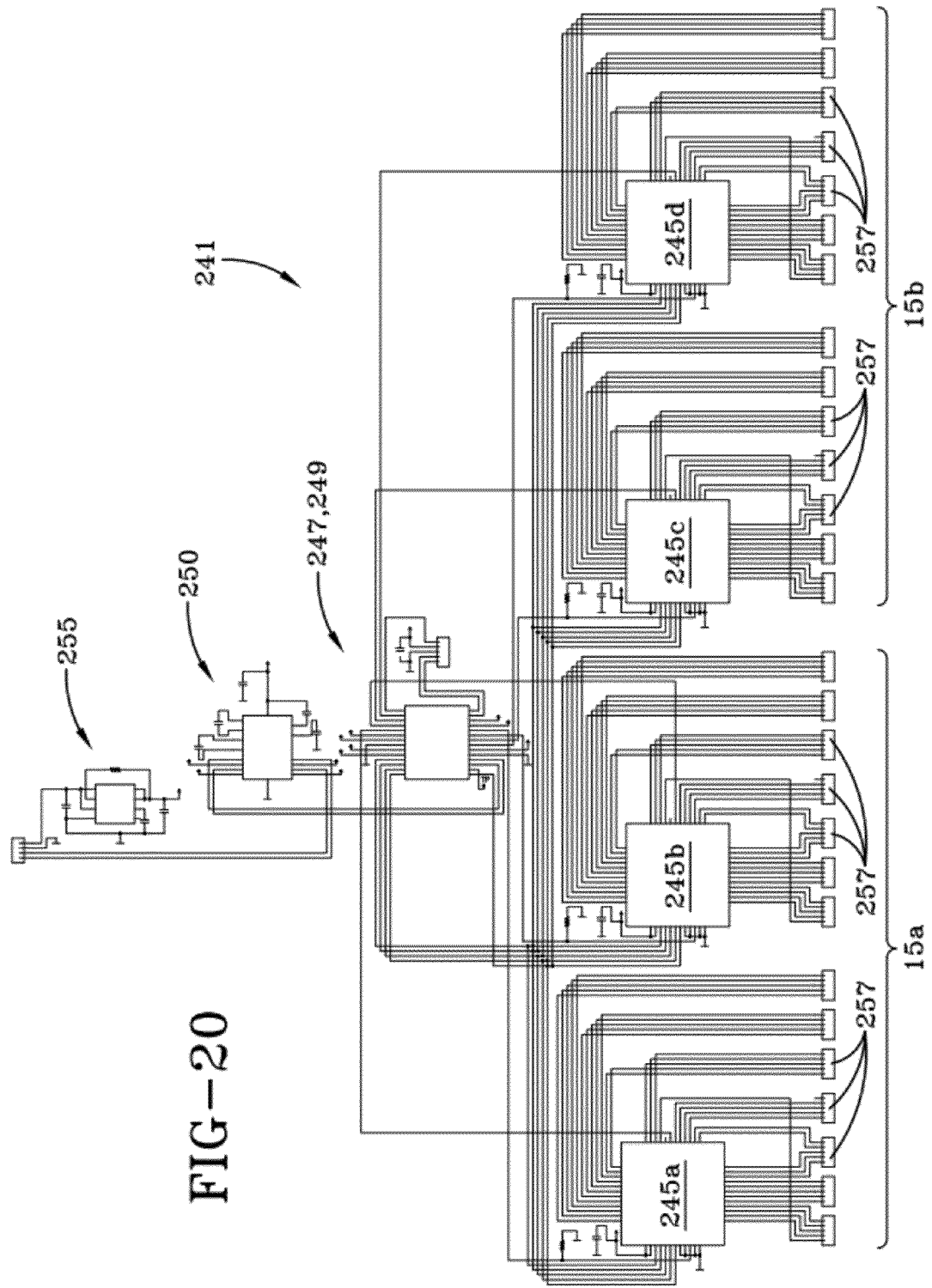
FIG. 20 is a detailed schematic diagram of a portion of the illustrative sensor data acquisition and processing system of FIG. 19.

Additional details of an exemplary sensor data acquisition and processing system 241 are shown in FIGS. 19 and 20 as including many of the features of the system 12 detailed above in connection with FIG. 1. More particularly, FIG. 19 is a detailed block diagram of a portion of the damage detection and remediation system 10 of FIG. 1, showing illustrative sensor data acquisition and processing system 241 coupled to sensing device 243, while FIG. 20 is a detailed schematic diagram of a portion of the illustrative sensor data acquisition and processing system 241 of FIG. 19. Sensing device 243 may be of any type further detailed herein, for example sensing device 14.

As shown in FIGS. 19 and 20, the measurement system 20 may include a multiplexer 245 (shown as a plurality of interconnected multiplexers 245A-245D in FIG. 20) coupled to a sensor array or sensing device 243 and a measurement device 247. The impact detection processing system 30 may include a micro-controller 249 coupled to the multiplexer 245 and the measurement device 247. The micro-controller 249 is illustratively coupled to user interface 50 and memory 31. A communication device 250 may operably couple the micro-controller 249 with the user interface 50 and/or a main computer 261.

FIG. 20 shows representative sensor data acquisition and processing system 241 configured to be used in connection with illustrative sensing device 14, 243 of the type detailed above. A plurality of electrical connections 257 operably couple multiplexers 245A and 245B with sensing layer 15a (FIG. 3), and operably couple multiplexers 245C and 245D with sensing layers 15b (FIG. 3). It should be appreciated that additional multiplexers 245 may be coupled to sensing layers 15a and 15b, or to at least one additional sensing layer 15c (FIG. 3). A voltage regulator 255 may be in electrical communication with the micro-controller 249 and illustratively provides a consistent stepped-down voltage (e.g., from a 24 volt input to 5 volt output).

The operation of this exemplary sensor data acquisition and processing system 241 is further explained in connection with FIGS. 19 and 20. The sensor arrays 243 are illustratively connected to the measurement and data acquisition and processing system 241 in order to provide feedback to user interface 50. This sensor data acquisition and processing system 241 may utilize multiplexer 245 connected to a micro-controller 249 to cycle through one, more than one, groups, or successive sensor elements on selected or every sensor array 243 or sensor array 243 layer. The multiplexer 245 is illustratively connected to measurement device 247 to check each sensor array 243. Data from one or more sensing arrays 243 are sent back to the microcontroller 249 for network data logging and data processing, and potentially for display via the user interface 50.

Figure 21:
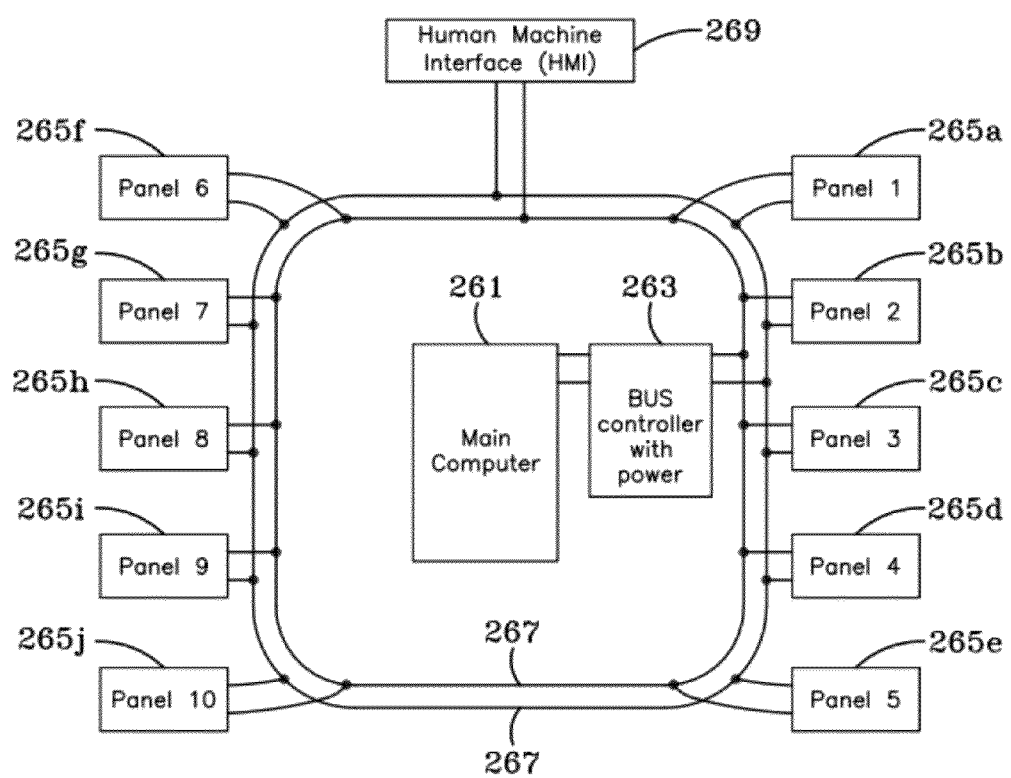
FIG. 21 is a block diagram of an exemplary system including a plurality of sensing devices and processing systems operably coupled to a main computer through an electrical bus.

FIG. 21 shows an exemplary system in accordance with the disclosure which includes a plurality of data acquisition and processing systems. In this example, approximately ten impact sensor arrays 265a-265j, illustratively together with associated measurement systems 20 and damage detection processing systems 30, are coupled to an electrical bus 267. In one illustrative embodiment, the bus 267 may comprises a CAN (Controller Area Network). The sensor arrays 265 may each comprise any one of those further detailed herein, such as impact sensing device 14, 149, 191, or 211. In one illustrative embodiment, these exemplary impact sensor arrays 265a-265j each include a microcontroller and a resistance measurement system. The bus 267 is coupled with a controller 263 which includes a power supply. A main computer 261 or processing system is coupled to the controller 263 which processes information sensed through the impact sensor arrays 265a-265j. A human machine interface (HMI) 269 provides information on impact events to a user.

Figure 22:
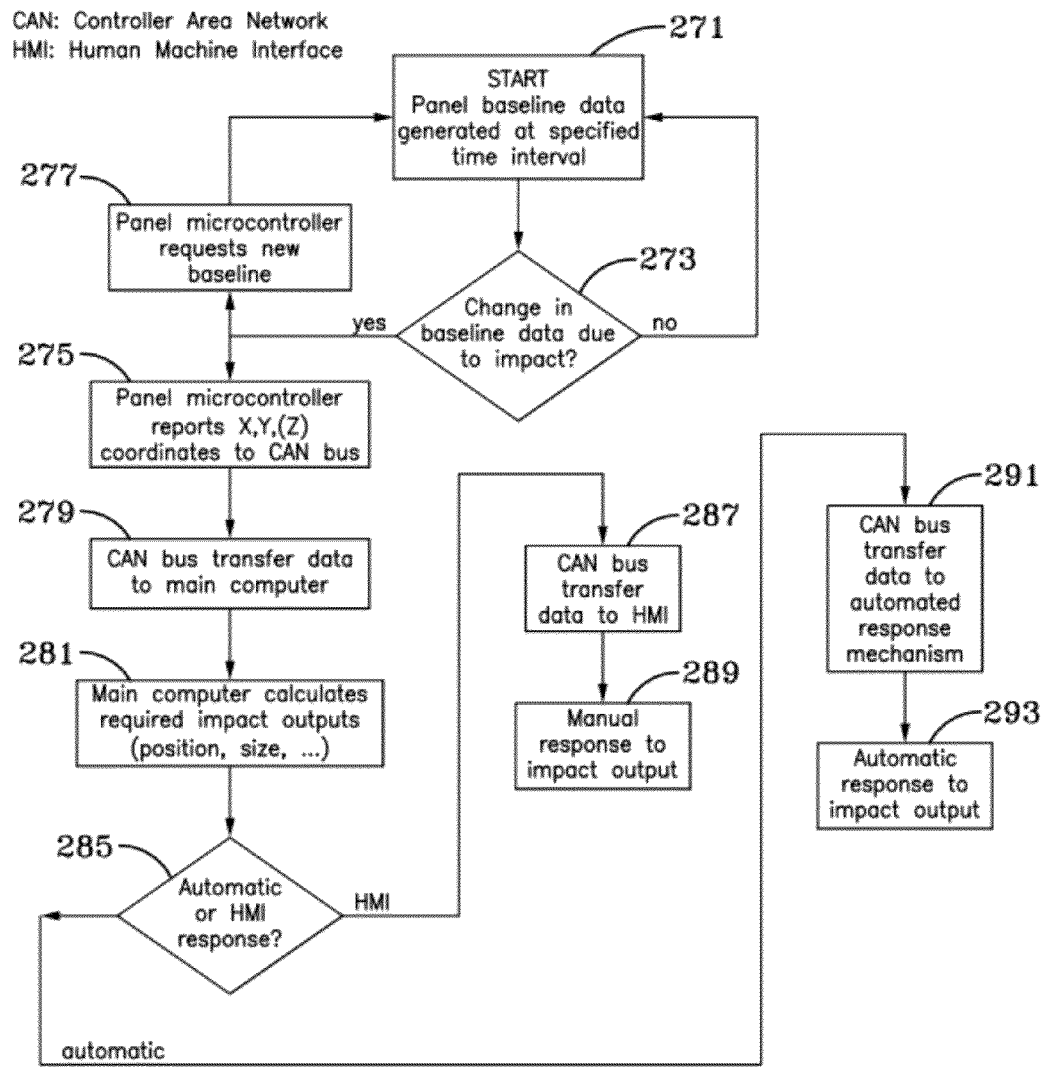
FIG. 22 is a flow chart of an exemplary method of operation in accordance with an illustrative embodiment of the disclosure.

FIG. 22 shows an exemplary method of operation for an illustrative impact detection and remediation system 10 in accordance with one embodiment of the disclosure such as, for example, that used in connection with the sensing device or panel 14 of FIG. 3. At step 271, processing system 12 in accordance with one embodiment of the disclosure generates panel baseline data at a specified time interval. More particularly, the measurement system 20 monitors the sensing device or panel 14 and supplies representative data to the damage detection processing system 30 which establishes the panel baseline data and stores it in memory 31. In one illustrative embodiment, the baseline measurement data determination is based on a predetermined data value associated with a state of layer assembly 15 by taking an electrical signal measurement before the damage event 13. Illustratively, this may be accomplished by the measurement system 20 monitoring the conductive paths defined by traces 5 (i.e., measuring portions) of layer assemblies 15a, 15b, 15c between respective contacts 7 and 9, as further detailed herein.

At step 273, the processing system then compares the currently generated data from the initial baseline generation produced from step 271, if the data has changed this signals that an impact event has occurred, and the process then simultaneously moves to steps 277 and 275. The currently generated data comprises measurements from monitoring the conductive paths defined by traces 5 (i.e., measuring portions) of layer assemblies 15a, 15b, 15c reported at a predetermined basis. The predetermined basis may include a fixed time interval or an input event, such as a temperature change.

At step 275 of FIG. 22, the panel 14 reporting the impact sends X, Y, Z coordinate data via a CAN (Controller Area Network) bus 267. As further detailed herein, the X, Y, Z coordinate data may be determined by comparing different adjacent traces 5 (i.e., measuring portions), for example in different layer assemblies 15a, 15b, 15c. It should be noted that a CAN system is one form of a communication or network system which may be used. Other communication or networking systems may be used to perform the function of facilitating control signals between systems or components. At step 277, the panel's microcontroller or measurement system 20 requests a new baseline via the CAN bus 267 from the processing system 30, thus resetting the baseline data to the current scenario in order to detect a new impact event. At step 279, the CAN bus 267 may transfer the coordinate data from step 275 to the processing system 30. At step 281, the processing system 30 illustratively calculates data including the impact locations, sizes, time data of the damage event, and corresponding damage assessment (e.g. a category of the damage event), and sends this data to HMI (Human Machine Interface) system 269 and/or a controller 261 for an automated response such as orienting an output device 90, such as a sensor or weapon, on an axis 21 aligned with an impact event origin area 17.

The category of the damage event may include a plurality of causes of the damage event which are correlated with at least one damage event characteristic. The plurality of causes may include a small arms category (e.g. 3 mm to 8 mm projectiles), an explosively formed penetrator category, high energy ballistic impact category (e.g., micro meteoroids or space debris impacts), a structural fatigue category, a heat event category, and a .50 or larger caliber projectile category.

Continuing with step 285 of FIG. 22, a determination is made based on input from step 281 for an automatic or HMI response which then triggers additional processing steps associated with the respective automatic or HMI response. The step 285 processing system responds to inputs from step 281 based on pre-programmed conditions. At step 287, an HMI command input for an HMI triggered event is sent via the CAN bus 267 to an HMI device after a determination at step 285 that a manual response output may be required based on determinations made at step 281. At step 287, data from step 281 based on the determination at step 285 is transferred onto the CAN bus 267 and sent to the HMI device 269 in order to notify a user of the potential need for the manual response output. At step 289, the manual response output determined from step 285 is executed based on a user input directing execution of the manual response output. Note that a user may decline to execute the manual response output as well after the user has been notified of the need for a decision on whether to execute the manual response output. The HMI system 269 via the CAN bus 267 may control devices coupled directly to the CAN bus 267 such as a weapon, sensor system, a communication system, a non-lethal weapon system, a display system, or other device a user will desire to manually trigger via a manual response output signal. An alternate embodiment may have the HMI system 269 interacting via a bus system with a controller system or a cloud computing system in communication with the HMI system 269.

At step 291, an automatic response is input in the CAN bus 267 after a determination is made at step 285 that an automatic event is required based on data from step 281. At step 293, the automatic event from step 285 is executed based on the determination at step 285 and the automatic event data from step 291.

Figure 23:
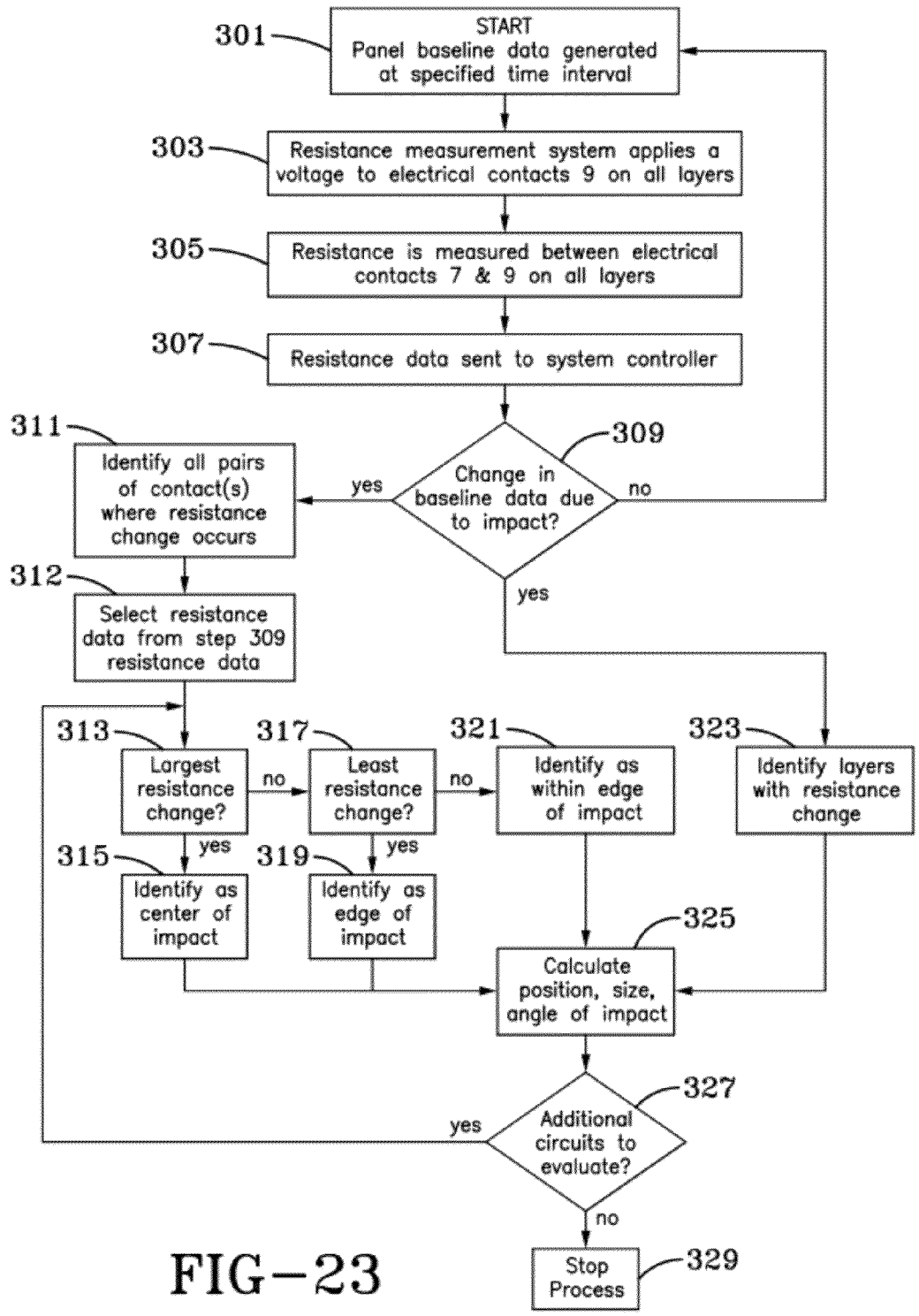
FIG. 23 is a flow chart of a further exemplary method of operation in accordance with an illustrative embodiment of the disclosure.

FIG. 23 shows an alternative method of operation for an illustrative impact detection and remediation system 10 such as, for example, that used in connection with the sensing device or panel 14 of FIG. 3, and the data acquisition and processing system 241 of FIGS. 19-21. At step 301, processing system 12 commences operation and one or more impact sensor panel baseline data is generated at specified time intervals. Impact sensor panel 14 baseline data may include resistance values for sections of the impact sensor panel such as all discrete circuits (e.g., 5 in FIG. 3) on each impact sensor panel. At step 303, a resistance measurement system applies a voltage to electrical contacts (e.g., 9) on all layers (e.g., 15a, 15b, 15c) making up a panel 14. As detailed herein, panel 14 may be formed of one or more layers 15a, 15b, 15c. At step 305, the resistance measurement system measures electrical resistance between all contacts (e.g., 7, 9) on all layers (e.g., 15a, 15b, 15c). At step 307, resistance data produced by the resistance measurement system is sent to a system controller via a bus system (e.g., CAN bus 267 from FIG. 21).

At step 309 of FIG. 23, a determination is made of whether the resistance measurement data acquired at step 305 is different than baseline data acquired at step 301 or stored previously. At step 311 all pairs of contacts (e.g., 7, 9) are identified on each layer (e.g. 15a, 15b, 15c) where resistance data has changed from the baseline data if the determination at step 309 determines the resistance measurement data is different and resistance change data is stored associated with an identifier associated with each discrete circuit (e.g., 5) between the pairs of contacts (e.g., 7, 9). At step 323, processing continues by identifying all layers (e.g., 15a, 15b, 15c) associated with the changed resistance data associated with pairs of contacts where resistance changed occurred that was determined at step 309 then processing continues at step 325.

At step 312, one of the resistance data is selected from the resistance data stored at step 309. At step 313, all resistance change data associated with each discrete circuit stored at step 309 is compared to a selected resistance data associated with one of the discrete circuits selected at step 312 and a determination is made of whether the selected resistance data has the largest resistance value change from the baseline data as compared to all resistance data stored at step 309. At step 315, if the determination at step 312 is the selected resistance data has the largest resistance value change, then the selected resistance data is associated with a center point identifier data at step 315 indicating a center point or area of an impact event then processing continues at step 325. If the selected resistance data is found to not to have the highest resistance change among the resistance data collected at step 309, then processing continues at step 317.

With reference to step 317 of FIG. 23, all resistance change data associated with each discrete circuit stored at step 309 is compared to a selected resistance data associated with one of the discrete circuits selected at step 312 and a determination is made of whether the selected resistance data has the least resistance value change from the baseline data as compared to all resistance data stored at step 309. At step 315, if the determination at step 312 is the selected resistance data has the least resistance value change, then the selected resistance data is associated with an edge of the impact area data at step 319 indicating an edge point or area of an impact area event in the impact sensor panel then processing continues at step 325. If the selected resistance data is found to not to have the least resistance change among the resistance data collected at step 309, then processing continues at step 321. At step 321, the selected resistance data and associated discrete circuit is associated within an impact event edge area but not a center of impact area then processing continues at step 325. At step 325, a calculation of position, size, angle of impact is determined from data from steps 315, 319, 321, and 323 then processing continues at step 327. At step 327, a determination is made of whether any of the resistance data associated with discrete circuits determined and stored at step 309 has not been selected at step 313 and subsequently processed in steps 313-325. If yes, then processing continues from step 327 at step 312. If no, then processing from step 327 terminates at step 329.

Figure 24:
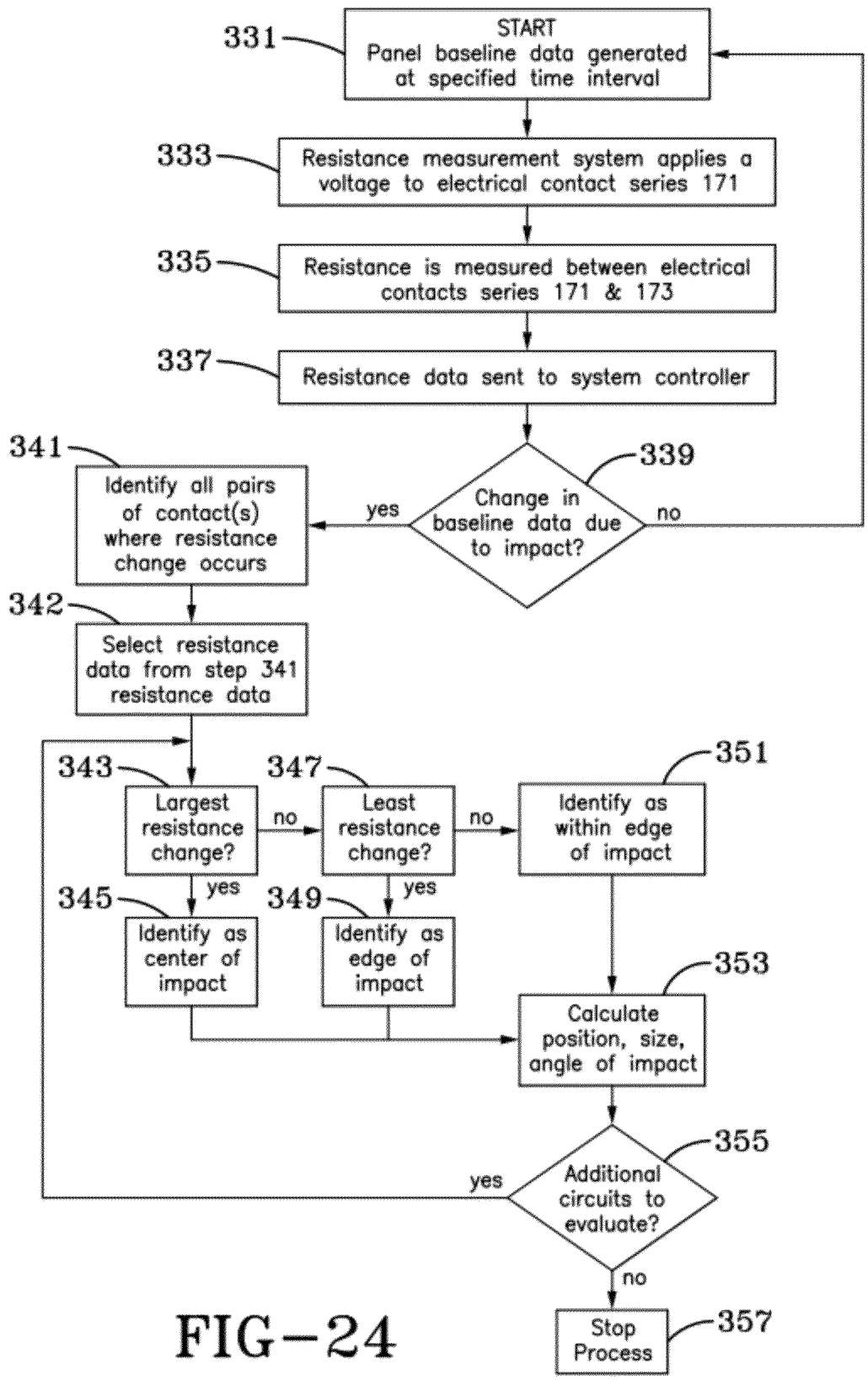
FIG. 24 is a flow chart of a further exemplary method of operation in accordance with an illustrative embodiment of the disclosure.

FIG. 24 shows an alternative method of operation for an illustrative impact detection and remediation system 10 such as, for example, that used in connection with the sensing device or panel 149 of FIGS. 8 and 9, and the data acquisition and processing system 241 of FIGS. 19-21. At step 331, processing the system 12 commences operation and one or more impact sensor panel baseline data is generated at specific time intervals. Baseline data of impact sensor panel 149 may include resistance values for sections of the impact sensor panel such as all discrete circuits (e.g., 155 and 157 in FIG. 8) on each impact sensor panel. At step 333, resistance measurement system applies a voltage to electrical contacts (e.g., 171) making up panel 149. At step 335, the resistant measurement system measures electrical resistance between all contacts series (e.g., 171 and 173). At step 337, resistance data produced by the resistance measurement system is sent to a system controller via a bus system (e.g., CAN bus 267 from FIG. 21).

At step 339 of FIG. 24, a determination is made of whether the resistance measurement data acquired at step 335 is different than baseline data acquired at step 331 or stored previously. If not, then the process returns to step 331. If there has been a change in baseline data at step 339, then the process continues to step 341 where all pairs of contacts (e.g., 171 and 173), are identified where resistance data has changed from the baseline data. At step 342, one of the resistance data is selected from the resistance data stored at step 341.

At step 343, all resistance change data associated with each discrete circuit stored at step 341 is compared to a selective resistance data associated with one of the discrete circuit selected at step 342 and a determination is made of whether the selected resistance data has the largest resistance value change from the baseline data as compared to all resistance data stored at step 341. At step 345, if the determination at step 342 is the selected resistance data has the largest resistance value change, then the selected resistance data is associated with a center point identifier data at step 345 indicating a center point or area of an impact event, processing then continues at step 353. If the selected resistance data is found to not to have the highest resistance change among the resistance data collected at step 341, then processing continues at step 347.

With reference to step 347 of FIG. 24, all resistance change data associated with each discrete circuit stored at step 341 is compared to a selected resistance data associated with one of the discrete circuits selected at step 342 and a determination is made of whether the selected resistance data has the least resistance value change from the baseline data as compared to all resistance data stored at step 341. At step 349, if the determination at step 342 is the selected resistance data has the least resistance value change, then the selected resistance data is associated with an edge of the impact area data at step 349 indicating an edge point or area of an impact area event 13 in the impact sensor panel 149 then processing continues at step 353. If the selected resistance data is found to not have the least resistance change among the resistance data collected at step 341, then processing continues at step 351. At step 351, the selected resistance data and associated discrete circuit is associated within an impact event edge area but not a center of impact area then processing continues at step 353. At step 353, a calculation of position, size, angle of impact is determined from data from steps 345, 349, and 351 and processing continues at step 355. At step 355, a determination is made of whether any of the resistance data associated with discrete circuits is determined and stored at step 341 has not been selected at step 343 and subsequently processed in steps 347, 349, 351, 353. If yes, then processing continues from step 355 at step 343. If no, then processing from step 355 terminates at step 357.

Figure 25:
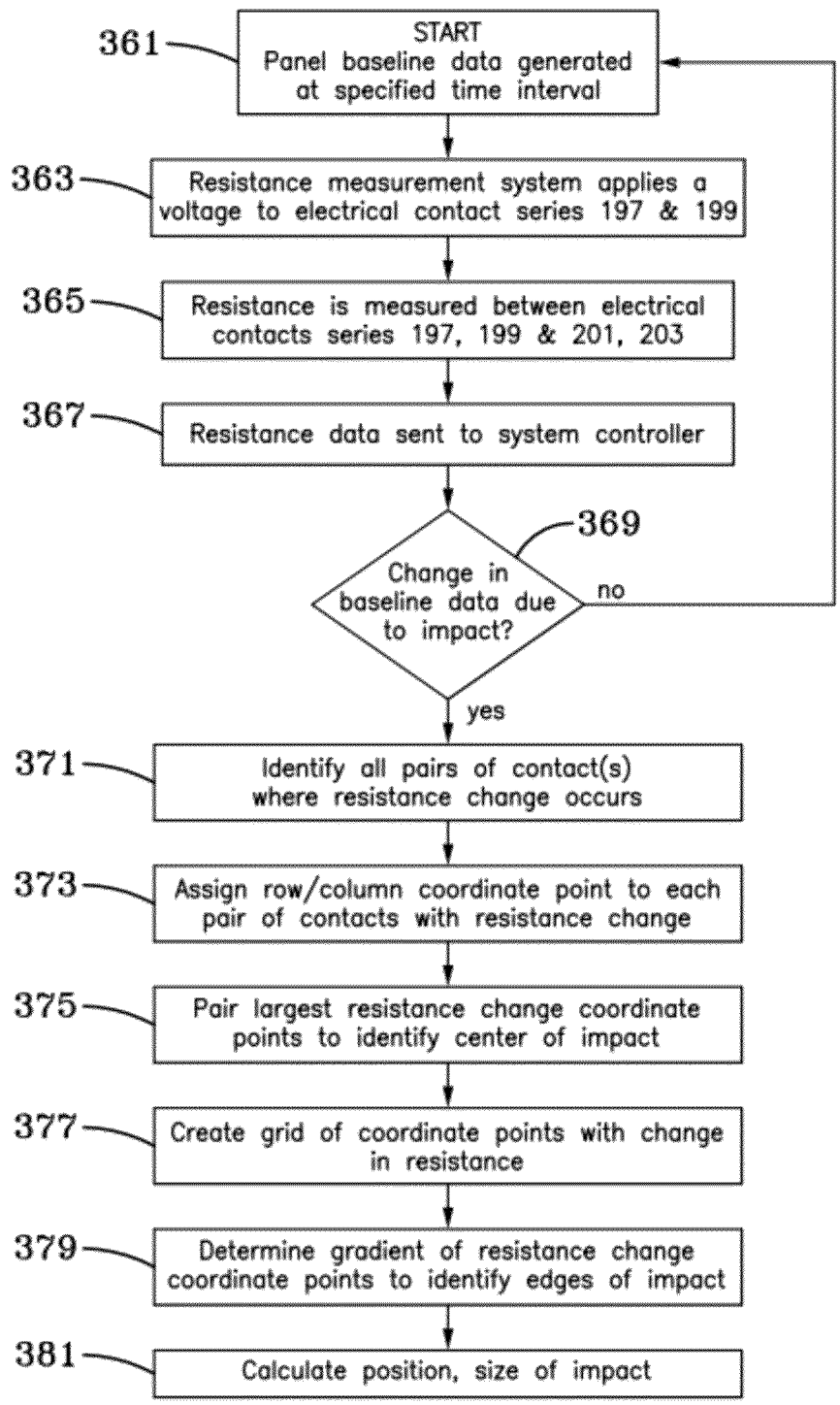
FIG. 25 is a flow chart of a further exemplary method of operation in accordance with an illustrative embodiment of the disclosure.

FIG. 25 shows an alternative method of operation for an illustrated impact detection and remediation system 10 such as, for example, that used with the illustrative sensing device or panel 191 of FIG. 10 and the data acquisition and processing system 241 of FIGS. 19-21. At step 361, processing system 12 commences operation and one or more impact sensor panel baseline data is generated at specific time intervals. Impact sensor panel 191 baseline data may include resistance values for layer of sensor panel 191. At step 363, a resistance measurement system applies voltage to electrical contact series 197 and 199 making up panel 191. As detailed herein, panel 191 may be made up of a great resistant panel. At step 365, the resistance measurement system measures electrical resistance between electrical contact series 197, 199 and 201, 203. At step 367, resistance data produced by the resistance measurement system is sent to a system controller via a bus system (e.g., CAN bus 267 from FIG. 21).

At step 369 of FIG. 25, a determination is made of whether the resistance measurement data acquired at step 365 is different than baseline data acquired at step 361 or stored previously. If not, then the process returns to step 361. If there is a change in the baseline data determined at step 369, then the process continues to step 371 where all pairs of contacts are identified where resistance data has changed from the baseline data if the determination at step 369 determines the resistance measurement data is different and resistance change data is stored associated with an identifier associated with each discrete circuit between the pairs of contacts. At step 373, processing continues by assigning a row and column coordinate point to each pair of contacts with a resistance change.

At step 375, the largest resistance change coordinate points to identify the center of the impact. At step 377, the process creates a grid of coordinate points having changes of resistance. At step 379, the system determines a gradient of resistance change coordinate points to identify edges of impact. Next, at step 381, the system calculates a position and the size of impact event 13.

Figure 26:
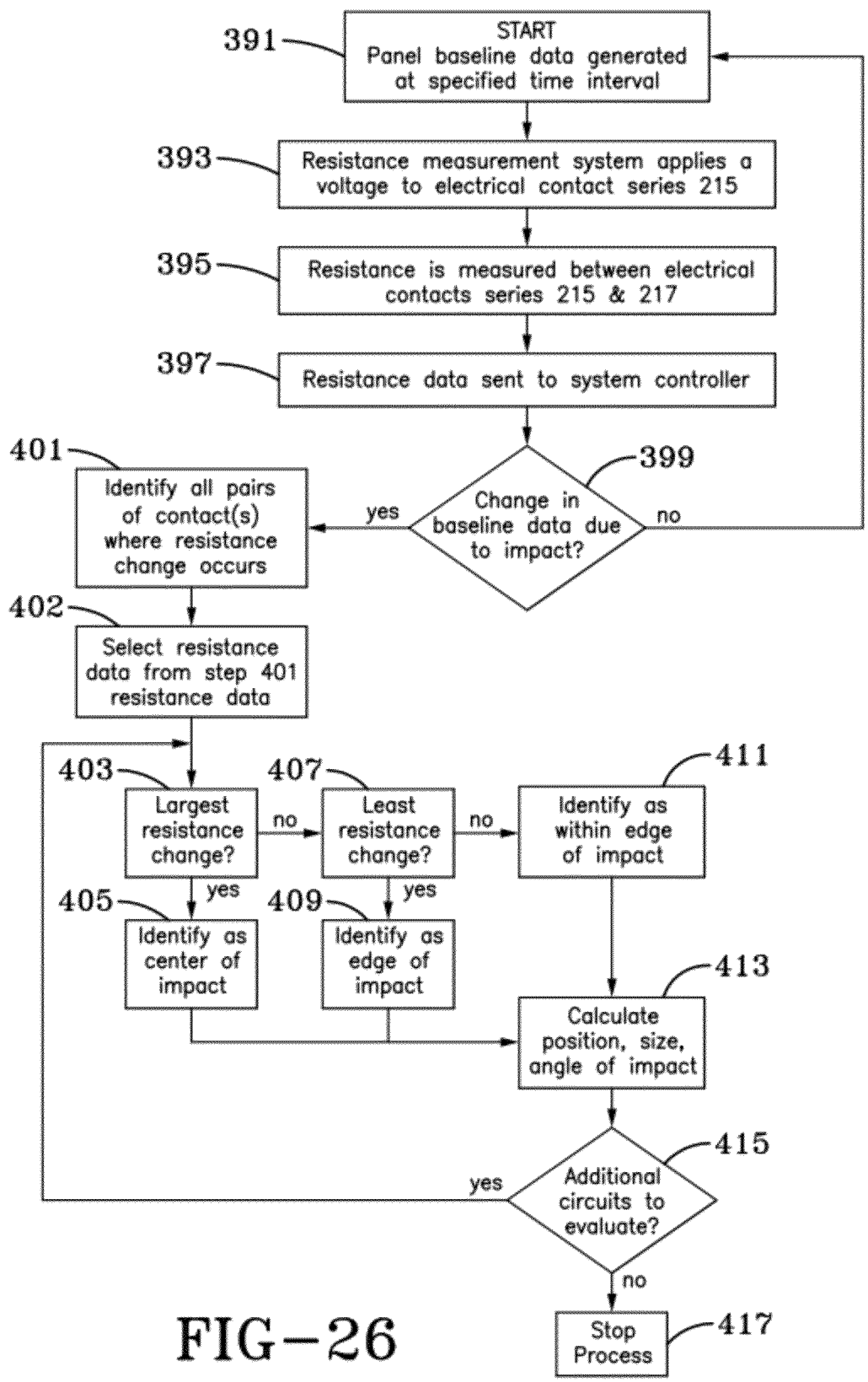
FIG. 26 is a flow chart of a further exemplary method of operation in accordance with an illustrative embodiment of the disclosure.

FIG. 26 shows a further method of operation of an illustrative impact detection and remediation system 10 such as, for example, that used in connection with the illustrative sensing device or panel 211 of FIG. 11 and the data acquisition and processing system 241 of FIGS. 19-21. At step 391, processing the system 12 commences operation and one or more impact sensor panel baseline data is generated at specific time intervals. Impact sensor panel 211 baseline data may include resistance values for sections of the impact sensor panel 211 such as on layer 213. At step 393, a resistance measurement system applies a voltage to electrical contacts 215 making up panel 211. As detailed herein, panel 211 may be made up of a gradient resistant layer. At step 395, the resistant measurement system measures electrical resistance between all contacts 215 and 217. At step 397, resistance data produced by the resistance measurement system is sent to a system controller via a bus system (e.g., CAN bus 267 from FIG. 21).

At step 399 of FIG. 26, a determination is made of whether the resistance measurement data acquired at step 395 is different than baseline data acquired at step 391 or stored previously. At step 401 all pairs of contacts 215 and 217 are identified where resistance data has changed from the baseline data if the determination step at 399 determines a resistant measurement data is different and resistance change data is stored associated with an identifier associated with each discrete circuit between the pair of contacts 215 and 217. At step 402, one of the resistance data is selected from the resistance data stored at step 401.

At step 403, all resistance change data associated with each discrete circuit stored at step 401 is compared to a selected resistance data associated with one of the discrete circuits selected at step 402 and a determination is made of whether the selected resistance data has the largest resistance value change from the baseline data as compared to all resistance data stored at step 401. At step 405, if the determination at step 403 is the selected resistance data has the largest resistance value change, then the selected resistance data is associated with a center point identifier data at step 405 indicating a center point or area of an impact event 13 then processing continues at step 413. If the selected resistance data is found to not to have the highest resistance change among the resistance data collected at step 401, then processing continues at step 407.

With reference to step 407 of FIG. 23, all resistance change data associated with each discrete circuit stored at step 401 is compared to a selected resistance data associated with one of the discrete circuits selected at step 402 and a determination is made of whether the selected resistance data has the least resistance value change from the baseline data as compared to all resistance data stored at step 401. At step 405, if the determination at step 402 is the selected resistance data has the least resistance value change, then the selected resistance data is associated with an edge of the impact area data at step 409 indicating an edge point or area of an impact area event in the impact sensor panel then processing continues at step 413. If the selected resistance data is found to not to have the least resistance change among the resistance data collected at step 401, then processing continues at step 411. At step 411, the selected resistance data and associated discrete circuit is associated within an impact event edge area but not a center of impact area then processing continues at step 413. At step 413, a calculation of position, size, angle of impact is determined from data from steps 405, 409, and 411 then processing continues at step 415. At step 415, a determination is made of whether any of the resistance data associated with discrete circuits determined and stored at step 401 has not been selected at step 403 and subsequently processed in steps 403-413. If yes, then processing continues from step 415 at step 402. If no, then processing from step 415 terminates at step 417.

An embodiment of a damage control system 16 of the present disclosure may entail use of an impact sensor array 243 on a system or microelectronics device which is coupled to a controller. As is known, the controller may reconfigure the system or a microelectronics device. For example, a damage control system embodiment may include an impact event sensor array 243, such as described herein, which couples with a damage control system. The damage control system is configured to receive a damage event input from the impact sensor system with impact event data such as, for example, coordinates and size of damage. The damage control system then may reassign functions in a damaged area of a microcontroller or control system. For example, the microcontroller may be a field programmable gate array (FPGA) which has the capacity to be reprogrammed after a damage event and still maintain functionality.

Figure 27:
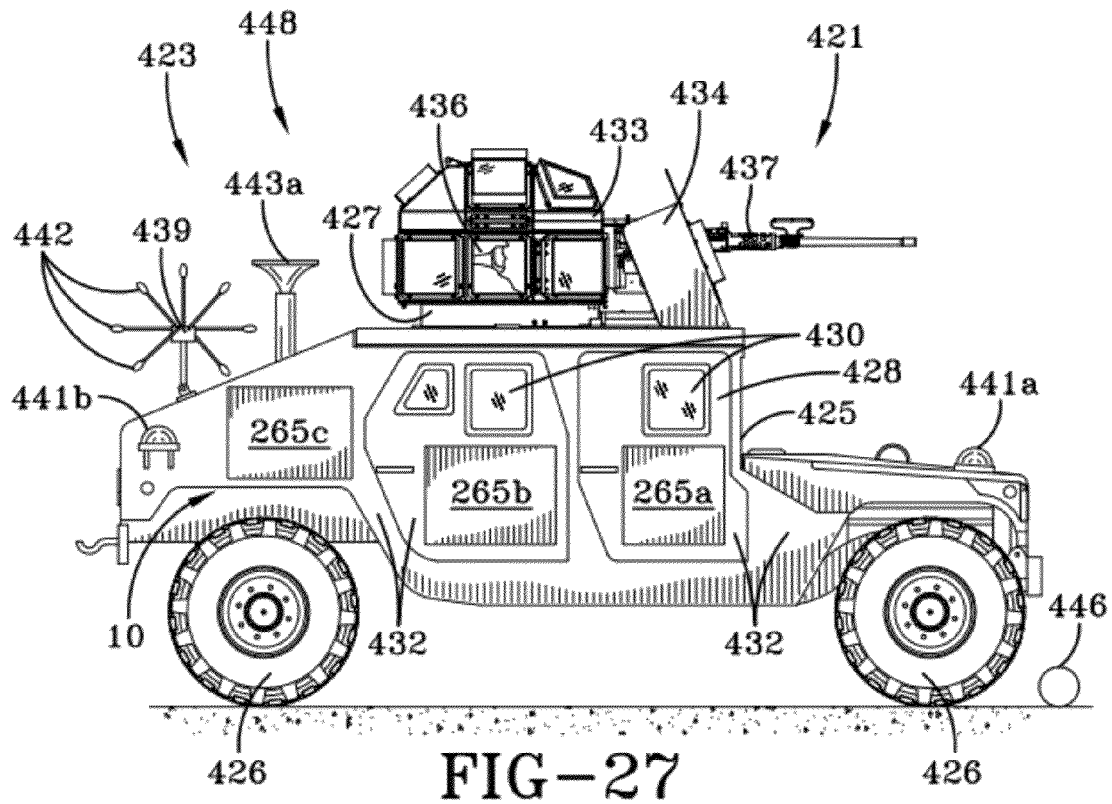
FIG. 27 is a side elevational view of an illustrative sensing device of the present disclosure used in connection with a vehicle and in cooperation with acoustical and image systems.
Figure 28:
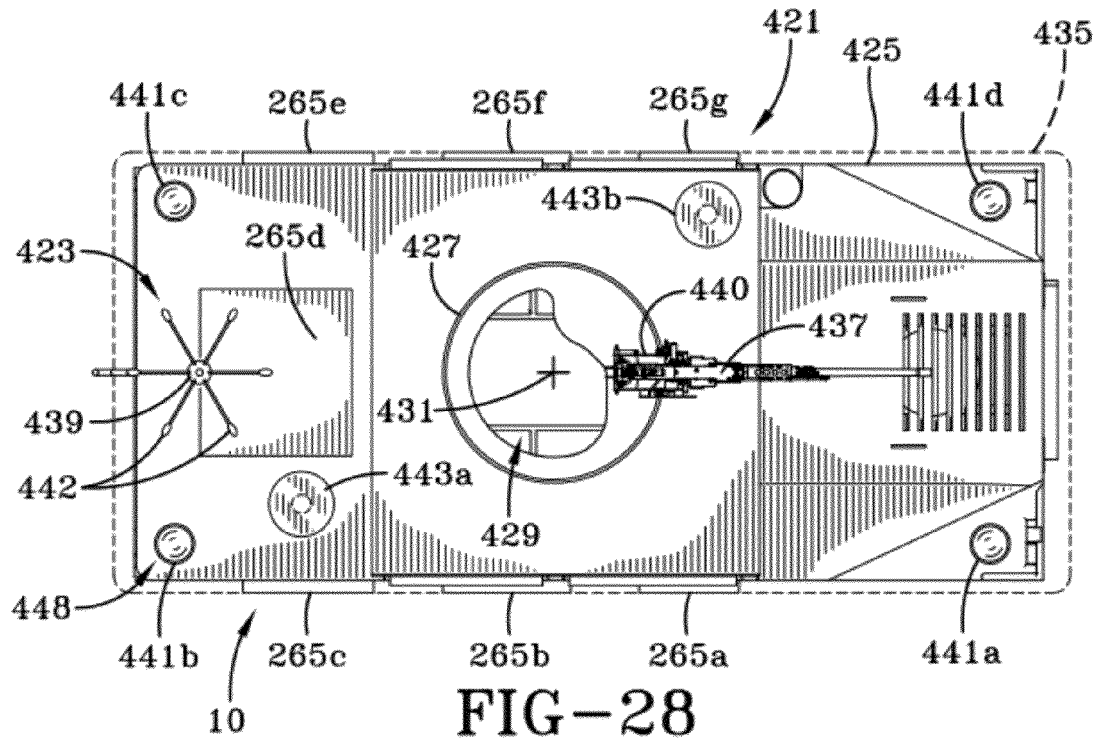
FIG. 28 is a top plan view of the vehicle of FIG. 27, with portions of the vehicle protective structure and user interface system removed for clarity.

With reference to FIGS. 27 and 28, the illustrative impact detection and remediation system 10 may also be coupled with other event detection systems or devices. For example, an event detection device, illustratively an escalation of force (EOF) reduction system 421, may include an embodiment of the impact detection and remediation system 10 coupled with an acoustic detection system 423 which is configured to detect specific sound signatures, such as a rifle shot. This illustrative EOF reduction system 421 is of particular use in a chaotic environment where multiple sound signatures exist but only one or a few of the sound signatures are significant. For example, illustrative EOF reduction system 421 may be used on a vehicle 425 forming part of a convoy maneuvering through a crowded urban area that have civilians who are not hostile to the convoy. A single person hiding in the crowd could fire a shot into the vehicle 425 in the convoy, which then may result in a number of external weapons being discharged, thereby confusing an observer or operator of the vehicle 425 as to the true source of the person firing a shot into their vehicle 425. An embodiment of the EOF reduction system 421 with the impact sensor system 10 and acoustic detection system 423 may be used to orient a vehicle operator to the direction (along origination axis 21 (FIG. 2)) where actual incoming fire is originating (origin 17 (FIG. 2)) and thereby reduce the potential for friendly fire casualties.

While the following description describes the impact sensor system 10 for use in connection with vehicle 425, as further detailed herein, the system 10 may find use in a variety of applications, including being mounted to other structures of interest 16, such as electronic devices, aircraft, etc. Further, the illustrative vehicle 425 in the embodiment of FIGS. 27 and 28 may be of any conventional type, such as military vehicles, law enforcement vehicles, rescue trucks, communications vehicles, and construction equipment. Illustratively, vehicle 425 may be a high mobility multipurpose wheeled vehicle (HMMWV or Humvee) including wheels 426 driven by an engine (not shown). An occupant compartment 428 including ballistic resistant windows 430 and armor plates 432 (FIG. 27).

In FIGS. 27 and 28, a plurality of sensing devices or panels 265 of the type detailed above are positioned in different locations around the vehicle 425. Each sensing device 265 may be coupled to an external or outer surface of the vehicle 425 in one of the manners further detailed herein. The combination of sensing devices 265 define an impact sensing perimeter 435 about the vehicle 425. For example, first sensing device 265a is positioned on an external surface of a front passenger door, second sensing device 265b is positioned on an outer surface of first rear passenger door, third sensing device 265c is positioned on an outer surface of a first rear quarter panel, fourth sensing device 265d is positioned on an outer surface of a rear deck, fifth sensing device 265e is positioned on an outer surface of a second rear quarter panel, sixth sensing device 265f is positioned on an outer surface of a second rear passenger door, and seventh sensing device 265g is positioned on an outer surface of a front driver door. It should be appreciated that the number and locations of sensing devices 265 may vary depending upon the structure of interest, operational requirements, environmental conditions, etc. Moreover, the plurality of sensing devices 265 may be consolidated such that a substantially continuous sensing surface extends around the exterior of the vehicle 425. As further detailed herein, a main computer 261 or processing system may be coupled to the controller 263 which processes information sensed through the impact sensing devices 265a-265g.

Figure 29:
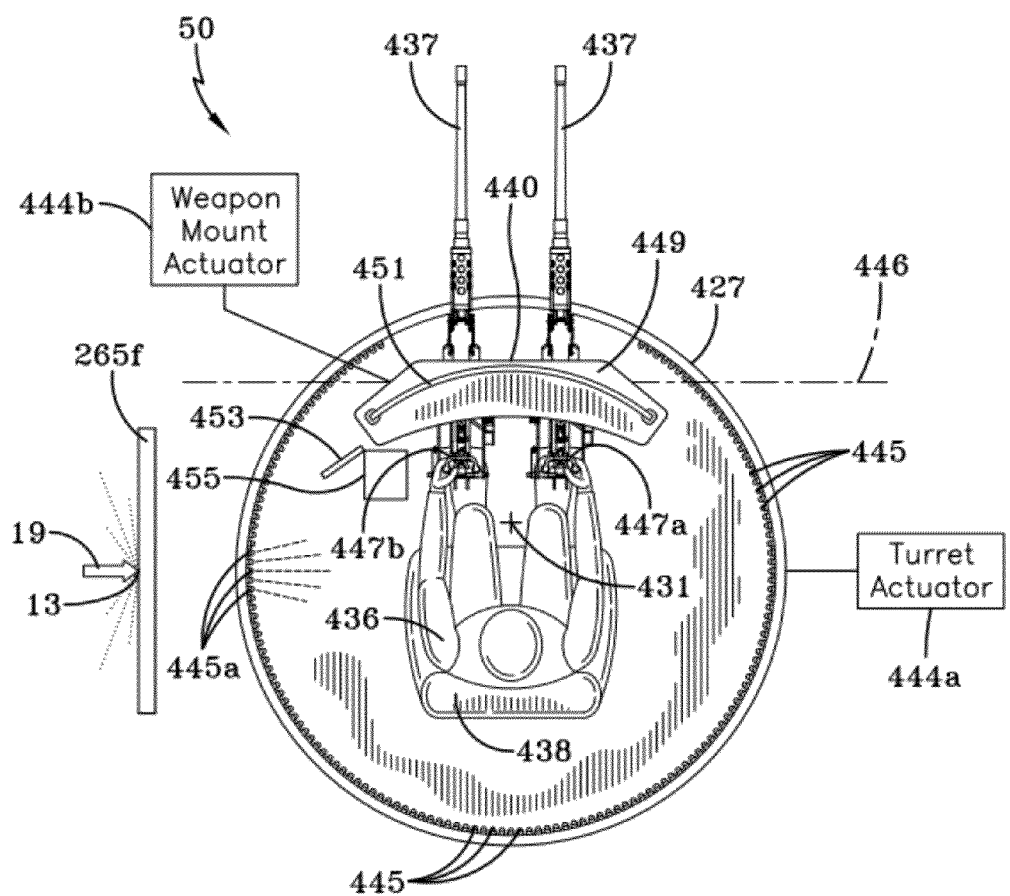
FIG. 29 is a partial top plan view of the vehicle of FIG. 27, showing an illustrative user interface system.
Figure 30:
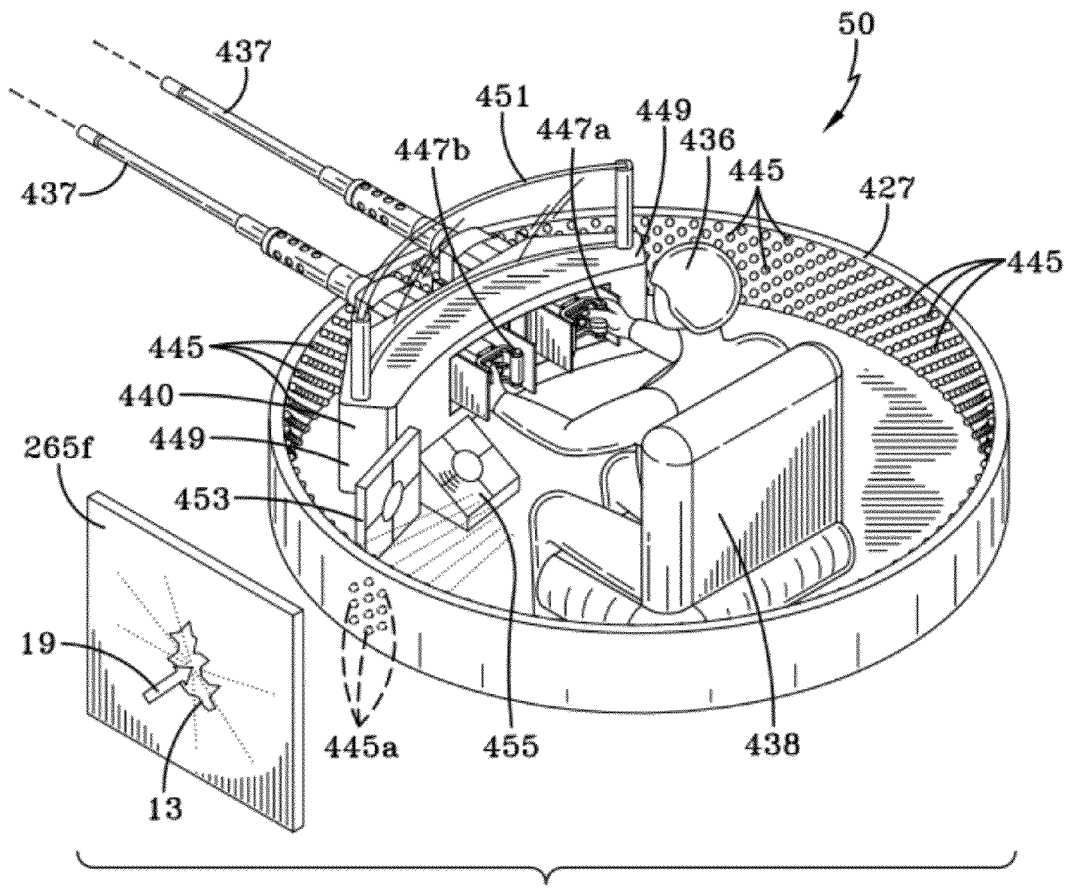
FIG. 30 is a top perspective view of the illustrative user interface system of FIG. 29.

The illustrative vehicle 425 includes a traversal portion, illustratively a rotatable turret 427 disposed around a center opening 429 (FIG. 28). As is known, the turret 427 is configured for rotation about a vertical rotational axis 431 extending through the opening 429. A protective structure 433 (FIG. 27) may be coupled to the turret 427. The protective structure 433 illustratively includes a plurality of ballistic windows coupled to a support structure for protecting an occupant or operator 436 within the opening 429. A protective shield 434 may be supported by the turret 427 in spaced relation to the protective structure 433. In the case of armed conflict, foreign internal defensive operations or riot control engagements, structure 433 may protect the operator or gunner 436 who controls a targeting device, such as a weapon 437, illustratively a machine gun or other device such as a water cannon, high intensity laser or other anti-personnel or non-lethal personnel weapon system. A seat 438 (FIG. 29) may be operably coupled to the turret 427 to rotate concurrently therewith and to support the operator 436 (FIG. 29).

The weapon 437 is operably coupled to a weapon mount 440 which, in turn, is operably coupled to the turret 427. A slewing mechanism 435 may adjust the horizontal (traverse or azimuth) and vertical (elevational) orientation of the weapon 437. As is known, rotation of the weapon 437 and about the vertical rotational axis 431 within a horizontal plane (i.e., traverse movement) may be controlled by operation of a turret actuator 444A (FIG. 29). The weapon mount 440 may also pivot the weapon 437 about a horizontal axis 446 and within a vertical plane (i.e., elevational movement). A weapon mount actuator 444B may be operably coupled to the weapon mount 440 to pivot the weapon 437 about the horizontal axis 446 (FIG. 29).

As is known, the slewing mechanism 435 may be operated remotely from the turret 427. Illustratively, the operator 436 may be positioned outside of the turret 427, for example within the passenger compartment of the vehicle 425 or at a location remote from the vehicle 425. In other illustrative embodiments, the slewing mechanism 435 may be automatically controlled by system 10 for alignment of the weapon 437 with origination axis 21, while discharge of the weapon 437 is controlled through a triggering device manipulated by operator 436 located outside of the turret 427.

With further reference to FIGS. 27 and 28, the illustrative acoustic detection system 423 may include an acoustic sensor or antenna 439 configured to detect soundwaves generated by an event, illustratively the firing of a projectile. The antenna 439 illustratively includes a plurality of audio inputs or microphones 442 (illustratively at least 3) configured in a known manner. More particularly, the microphones 442 are spaced apart from one another to detect and record acoustic signals or soundwaves, and time offsets of acoustic signals which are representative of the muzzle noise of the firearm and/or the soundwave emitted by a projectile. The detection system 423 is illustratively configured to process the signals and their time offsets in a manner for determining at least the direction in which the firearm of interest is located. In certain illustrative embodiments, the acoustic detection system 423 may comprise the Boomerang shooter detection system available from Raytheon BBN Technologies of Cambridge, Mass.

As also shown in FIGS. 27 and 28, additional sensors may also be used with the impact sensing devices 265 and/or acoustic sensor 439. For example, an imaging system 448 including a plurality of video surveillance sensors or cameras 441a, 441b, 441c, 441d may be positioned proximate opposing corners of the vehicle 425. Similarly, 360 degree video sensors or cameras 443a and 443b may be added to the vehicle 425. Cameras 441 and 443 may be adapted to detect weapon (e.g., rifle) fire flashes. More particularly, the cameras 441 and 443 may be used to detect flash events which are cross checked against data from the impact sensing devices 265 and/or the acoustical sensor 439. The EOF reduction system 421 may then cross correlate the information from the multiple sensor systems 265, 439, 448 thereby increasing the probability of accurate identification of hostile fire being directed towards a structure of interest, in this case vehicle 425 in a convoy.

Cameras 441 may include full motion video with zoom capability that may be moved or slewed to a point of origin of an impact event such as where a hostile person is directing rifle fire to a convoy vehicle 425. These video cameras 441 with zoom capability may then be used to gather specific evidence associated with the use of hostile force by a gunman in a crowded area by means of high definition video imagery which is oriented towards a point of origin 17 of an impact event 13. An illustrative embodiment of the system 10 may also include conflict resolution software or programming which permits it to deal with multiple impact events as well as providing instructions for focusing on higher priority significant event signatures and thus have the system 10 ignore inputs which are of lesser interest.

The user interface 50 may include a graphical user interface (GUI) providing information to a user to permit separate identification of different points of origin for different types of threats or impact events such as a different color in the GUI for each separate point of origin of an impact event, and a time delay which leaves an impact event indicator on for a predetermined period of time or a range of a point of origin area. A system may also be tied to a navigation system which suggests a route of egress from an area where impact events are occurring given terrain or obstacles which are in a particular area. For example, the system may have a map therewith (e.g., GOOGLE® maps) wherein the system 10 may overlay the map onto a video display of the impact events.

Characterization of impact event objects may be made based on multiple sensor systems. For example, a combination of an impact event sensor 265, acoustic sensor system 439, and a video imager system 448 may be used to correlate a source of an impact event based on a look up table having signature data associated with specific impact event originating devices or systems such as a particular type of rifle or projectile system.

Also, the multiple sensor variant may receive inputs from portable illumination beacons, or smart beacons 446, which are programmed to emit wireless coded signals which imaging system 448 including imager/360 degree camera 443 may detect (FIG. 27). These smart beacons 446 may be placed onto individual equipment, persons, or locations where friendly forces or equipment is located. The smart beacons 446 are illustratively capable of receiving a pulse of light in one or more frequencies and then trigger a burst signal which is not detectable by means such as humans viewing the system through night vision goggles, etc. The system 10 may interrogate the smart beacons 446 multiple times in order to ensure relative bearing and distance may be determined based on Doppler effect and changes in bearing. The smart beacons 446 may be cross referenced with other systems such as the GCCS 72.

Each smart beacon 446 may be programmed/provided with a verification system which permits verification that the user/wearer is in fact a friendly force. Such a verification system may include voice recognition for a single matched user, a proximity sensor for detecting an RFID system embedded into a larger system which has identity verification systems, or a coded input mechanism which a user may occasionally be prompted to input a verification code which then will unlock the smart beacon's verification capability.

Each smart beacon 446 is illustratively programmable and requires a user to input a new code to continue its operation past a certain amount of time, such as 24 hours. The smart beacon 446 may also have an anti-tamper design which would prevent directly reading the smart beacon's coded information. Also, the smart beacon 446 may have a self-wipe function which could be triggered by a user before the beacon 446 could fall into undesired hands. The self wipe function could also be triggered by a failure to reset the system in a certain number of hours such as 24 hours or after a substantial impact which causes damage to the smart beacon beyond a prescribed point.

Illustrative user interfaces 50 may include display devices operably coupled to the turret 427. In addition to visual indicators such as display devices, the user interface 50 may provide other sensory indicators to the operator 436. For example, an audible damage event warning may be provided to the operator 436 upon the detection of a damage event. The audible damage event warning may also provide details on the location of the damage event and/or an orientation of the damage event on the vehicle 425.

With reference now to FIGS. 29-32, the display devices may include a plurality of visual indicators arranged in a plurality of vertically spaced annular bands. Each annular band illustratively includes a plurality the circumferentially spaced light sources 445, each light source 445 being oriented radially inwardly from an inner arcuate surface of the turret 427. The light sources 445 may comprise light emitting diodes (LEDs), illustratively multi-color LEDs.

Activation of the light sources 445 is based upon input from the system 12 on the determined origin of the ballistic impact. More particularly, the system 12 may activate the light sources (identified by reference numbers 445a) based upon the relative position of the turret 427 in order to ensure that the light sources 445a are oriented along axis 21 toward the origin 17 of the projectiles/impact objects 19 (FIG. 2). Thus, when the turret 427 rotates, the active light sources 445a also move to maintain the relative bearing to the calculated point of origin 17 for the projectiles/impact objects 19. Such capability may be facilitated by operably coupling the user interface 50 into a position identifier system, such as a global positioning system (GPS), global command and control system (GCCS) 72, inertial navigation system, etc.

The active light sources 445a may change color, light intensity, and/or flash to assist the operator in identifying proper orientation of the turret 427. For example, the light sources 445a may change from red, to yellow, to green as the turret 427 is rotated into proper positioning with axis 21 of impact origin 17. Alternatively, the light sources 445a may change light intensity as the turret 427 is rotated into alignment with axis 21, or may flash at different rates as the turret 427 is rotated into alignment with axis 21.

The system 12 may also activate the light sources 445A based upon the relative elevation of the weapon 437 in order to ensure that the light sources 445a are oriented on the source of the projectiles/impact objects. Thus, when the weapon 437 is pivoted about axis, the active light sources 445a also move to maintain the relative bearing to the calculated point of origin 17 for the projectiles/impact objects 19 (FIG. 2).

In one illustrative embodiment, different vertically spaced bands of light sources 445a may be illuminated to indicate desired weapon elevation along axis 21. Alternatively, the color of the light sources may change based upon desired weapon elevation. The intensity or flashing rates of the light sources 445a may also change as the weapon 437 is pivoted into alignment with origination axis 21. In a similar manner, different circumferentially or horizontally spaced columns of light sources 445a may be illuminated to indicate desired traverse or horizontal position of weapon about vertical axis 431.

User inputs, such as right and left control grips 447a and 447b may be manipulated by the hands of an operator to move the weapon 437. The control grips 447a and 447b may each include input buttons to control traverse and elevation of the weapon 437 by controlling actuators 444a and 444b, as further detailed herein. Control grips 447a and 447b may also include conventional triggers to permit the operator 434 to fire the weapon 437. In certain illustrative embodiments, the control grips 447a and 447b may provide a tactile damage event warning which is sent to the operator 436. Such tactile event warning may provide an indication of a damage event alone or together with an orientation of the damage event on the vehicle 425. For example, the control grips 447a and 447b may vibrate or shake to alert the operator 436 of a damage event. Subsequent vibrating or shaking of the right control grip 447a will provide an indication to the operator 436 to move the weapon 437 to the right, while subsequent vibration or shaking of the left control grip 447b will provide an indication to the operator 436 to move the weapon 437 to the left.

A dashboard 449 may be supported by the weapon mount 440 and is positioned in front of the seat 438 for supporting the control grips 447a and 447b. The dashboard 449 is operably coupled to the turret 427 and is configured to rotate therewith. A heads-up display 451 may extend above the dashboard 449 and includes a transparent panel 452 having a surface upon which information is projected for view by the operator 434.

Figures 31, 32:
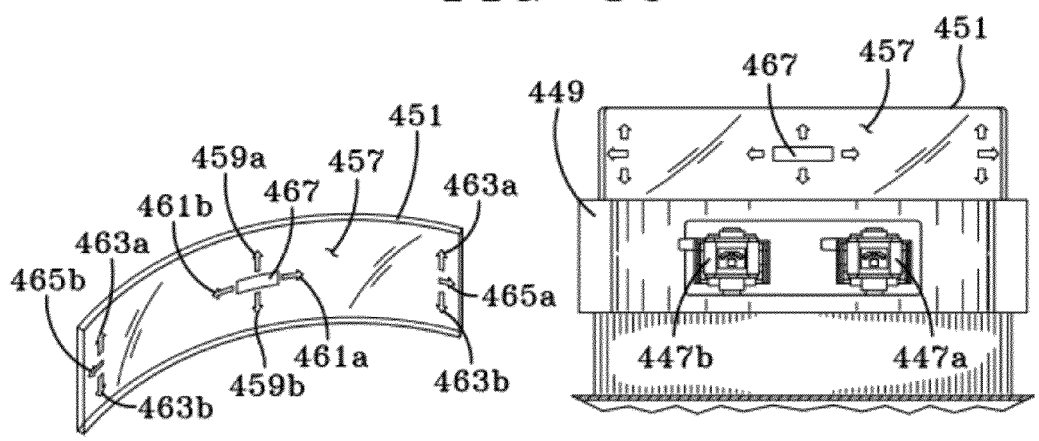
FIG. 31 is a front perspective view of a heads-up display of the user interface system of FIG. 30.
FIG. 32 is a front elevational view of the user interface system of FIG. 30.
Figure 33:
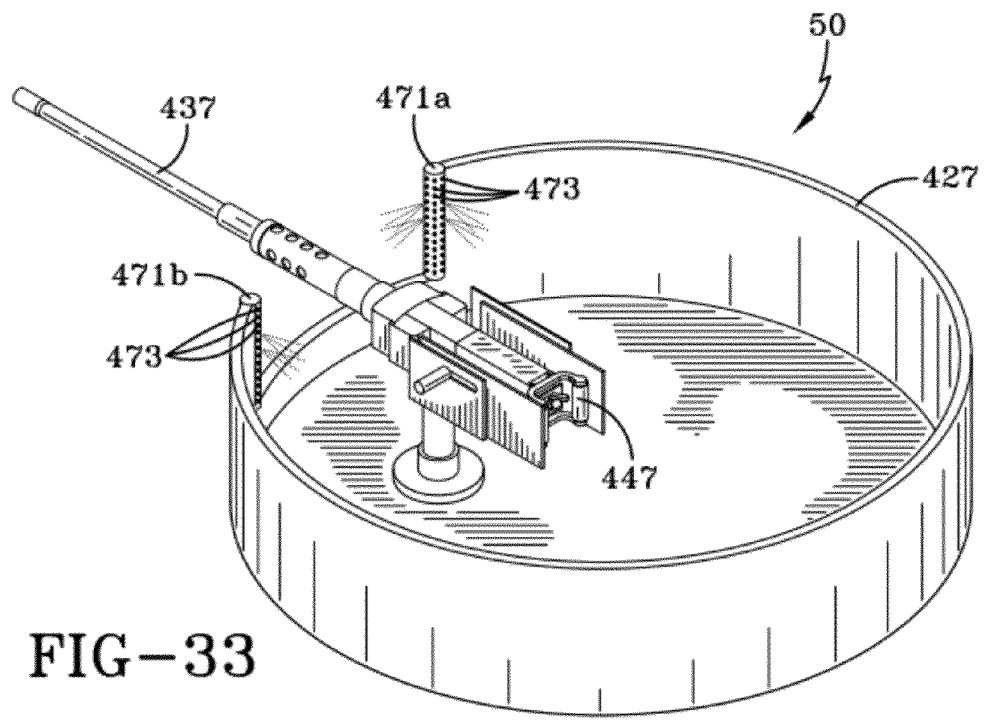
FIG. 33 is a top perspective view of a further illustrative user interface system.

With reference to FIGS. 31 and 32, different images 459, 461, 463, 465, 467 may be projected on the display 451. For example, images 459 and 463 may indicate to the operator 434 to change the elevation of the weapon 437 based upon the detected impact for alignment with origination axis 21. More particularly, images 459a and 463a indicate that the weapon 437 should be raised, while images 459b and 463b indicate that the weapon should be lowered. Similarly, images 461 and 465 may indicate to the operator 434 to traverse (move the rotational position of) the weapon 437 based upon the detected impact for alignment with origination axis 21. More particularly, images 461a and 465a indicate that the weapon should be rotated to the right, while arrows 461b and 465b indicate that the weapon should be rotated to the left. Information, such as video and/or text instructions may be projected within display window 467.

In certain illustrative embodiments, display 453 is operably coupled to the human machine interface (HMI) 269, while display 455 is operably coupled to the global command and control system (GCCS) 72. Displays 453 and 455 may provide graphical information and/or receive input from the operator.

A further illustrative embodiment is shown in FIGS. 33-35B as including turret 427 with the seat 438 removed for clarity. Circumferentially spaced right and left indicator uprights or columns 471a and 471b, respectively, are supported on opposite sides of turret opening 472 receiving weapon 437. Each indicator upright 471a and 471b includes a plurality of display devices arranged in a plurality of laterally spaced columns. More particularly, each upright 471a and 471b illustratively includes a plurality the vertically spaced light sources 473. The light sources 473 may comprise light emitting diodes (LEDs), illustratively multi-color LEDs.

Activation of the light sources 473 is based upon input from the system 12 on the determined origin of the ballistic impact. More particularly, the system 12 activates the light sources (identified by reference numbers 473a) based upon the relative position of the weapon 437 in order to ensure that the light sources 473a are oriented on the source of the projectiles/impact objects. Thus, when the elevation of the weapon 437 changes, the active light sources 473a also move to maintain the relative bearing to the calculated point of origin 17 for the projectiles/impact objects 19 (FIG. 2).

Rotational orientation of the turret 427 may be indicated by changing intensity, color, or flash patterns of light sources 473a. For example, green may indicate the proper direction in which to turn, while red means no adjustment is required. Alternatively, light intensity or flashing patterns of light sources 473a may indicate the proper direction in which to turn. Alternatively, additional displays may be used in combination with light sources 473 on uprights 471 to facilitate proper orientation of turret 427.

User inputs, such as control grips 447 may be manipulated by the hands of an operator to rotate turret 427, and thus the weapon 437. Control grips 447 may also include conventional triggers to permit the operator to fire the weapon 437.

Figure 34A:
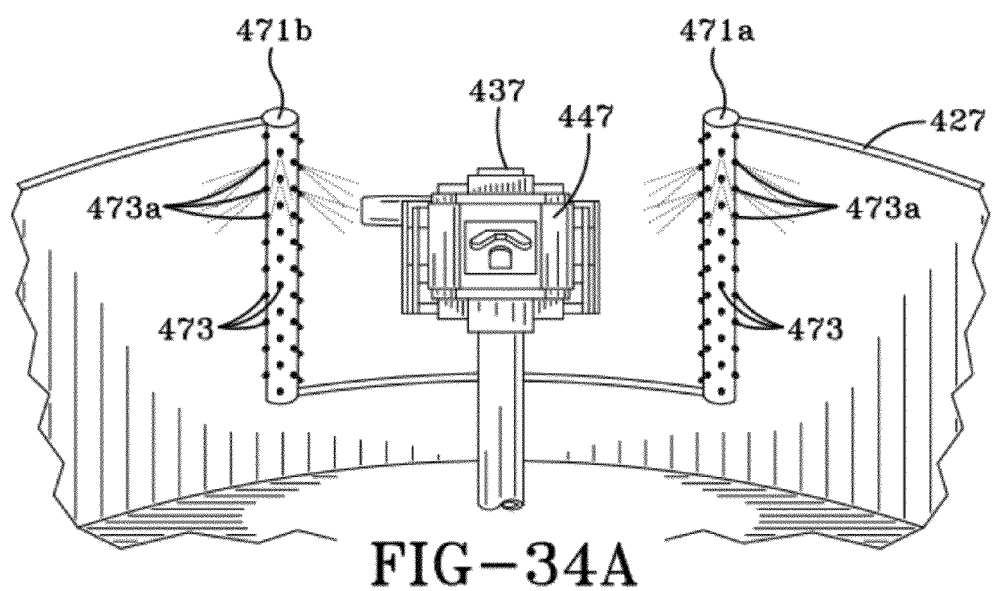
FIG. 34A is a front perspective view of the user interface system of FIG. 33, showing light sources illuminated to indicate the origin of an impact object above the current weapon elevation.

FIG. 34A shows a situation when the origin 17 of impact object is determined to be above the target alignment of the weapon 437. As such, the light sources 473a on an upper end of the indicator uprights 471 are activated. As the weapon 437 is raised, the active light sources 473a lower toward the middle of the uprights 471. At the proper target elevation (i.e., when the weapon 437 is aligned with origination axis 21), the light sources may change intensity, color, or flash to provide a clear indication to the operator that the proper target has been acquired.

Figure 34B:
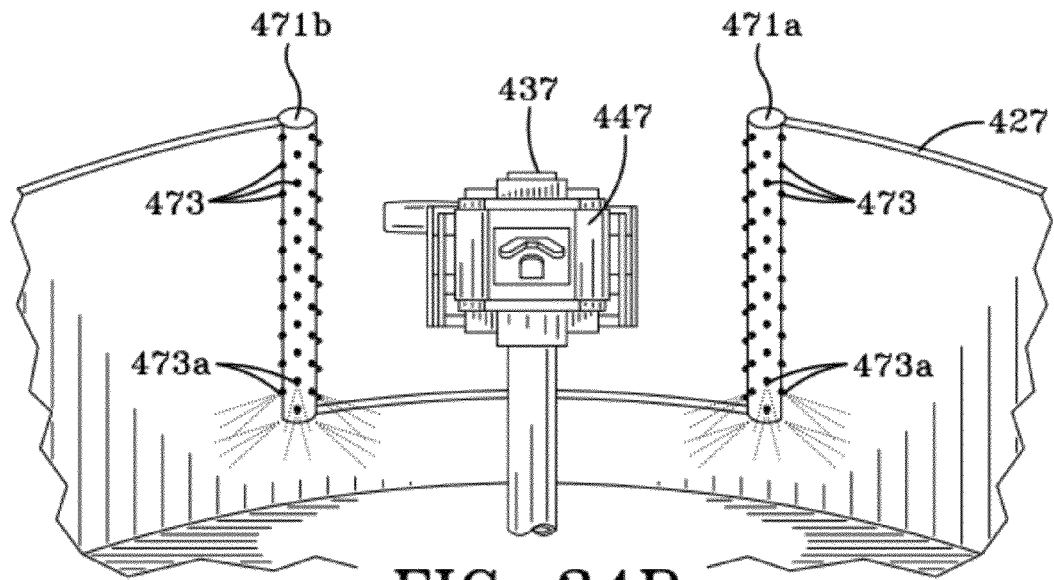
FIG. 34B is a front perspective view similar to FIG. 34A, showing light sources illuminated to indicate the origin of the impact object below the current weapon elevation.
Figure 34C:
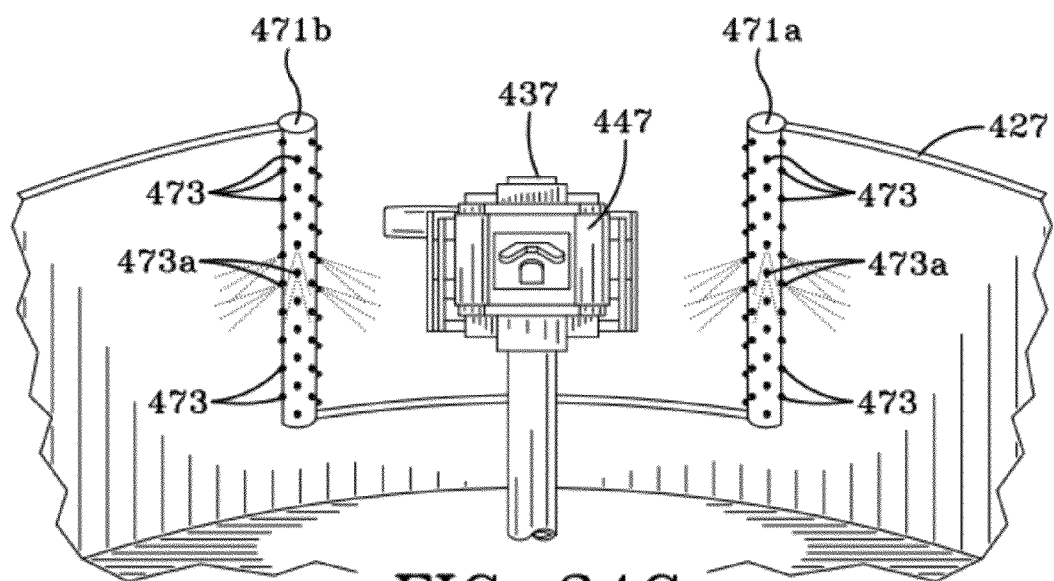
FIG. 34C is a front perspective view similar to FIGS. 34A and 34B, showing light sources illuminated to indicate the origin of the impact object aligned with the current weapon elevation.

FIG. 34B shows a situation when the origin 17 of impact object is determined to be below the target alignment of the weapon 437. As such, the light sources 473a on a lower end of the indicator uprights 471 are activated. As the weapon 437 is lowered, the active light sources 473a raise toward the middle of the uprights 471. At the proper target elevation (i.e., when the weapon 437 is aligned with origination axis 21), the light sources 473a may change intensity, color, or flash to provide a clear indication to the operator that the proper target has been acquired.

In certain illustrative embodiments, the computer 40 may include a timer configured to run upon detection of an impact event. The timer may cause the user interface 50 to reduce the impact event LED indicators 445, 473 to zero brightness following a predetermined time after a particular impact event. A user may engage an interface control to display historical impact information either on the LED indicators 445, 447 or on a video display. The video display history may be a video type replay showing a recreation of the impact events from a specific point in time to another point in time. For example, the video display may show an overhead image of a vehicle which is taking fire and the impact sensor is detecting fire. This vehicle display may be rotatable to show points of estimated origin relative to the vehicle and probable point of origin.

If the system 10 includes a video imaging system 448, having either full motion video and/or 360 degree cameras, then impact geometry and vector information may be overlaid over the video system based on plotting of coordinates and matching those coordinated to grid coordinate systems associated with the video camera and vehicle 425. A gun camera may also be added to a user's weapon system which may capture images of where a weapon 437 is being oriented. The gun camera may be utilized with the system for providing confirmatory information on impact event point of origin 17 information.

As further detailed herein, a feature of the user interface 50 may be a system which indicates elevation for an impact event point of origin 17. For example, LEDs may be run vertically along a weapon mount which flashes horizontal lines for where probable elevation of an impact event origin 17 is assessed. The weapon 437 may then be manually or automatically controlled to bring it into alignment with the axis of origin 21.

Further illustrative embodiments, exemplary damage detection and remediation system 10 may be coupled with a firing mechanism for a weapon 437 and a command and control system which has a position tracking feature, a status update feature, and is internetworked with other security force units, both fixed and mobile, such as the Global Command and Control System (GCCS) 72. When the firing mechanism is activated at the same time an impact event with matching characteristics of an attack occur then the exemplary embodiment of the damage detection and remediation system 10 may automatically post an update to the GCCS 72 that an attack is occurring in a specific location as well as clips from video systems, mounted with the weapon system, of the points of origin 17 of the attack. A panic button may be added to user interface 50 which may be used to confirm an attack which may then be posted to the GCCS 72 as a confirmation of attack in progress.

Another embodiment may include a damage detection and remediation system 10 which detects a pattern of attack damage or impact event which corresponds to an improvised explosive device (IED) attack which may then trigger an automatic request for assistance, with a location from a location tracking system such as the GCCS 72, and a request for medical evacuation absent an override command being input by a user.

In yet other illustrative embodiments of damage detection and remediation system 10, upon detecting damage events 13 in certain locations of the vehicle 425, onboard computers may run diagnostic tests of various vehicle systems. For example, if the system 10 detects that a damage event 13 has occurred in the engine compartment of the vehicle 425, then the onboard computer may run a diagnostic test of the vehicle's engine. Upon completion of the diagnostic test, the computer may transmit information regarding vehicle status to a fleet management computer at a vehicle maintenance facility. The fleet management computer may thereby keep track of damage sustain by various vehicles and schedule maintenance, as required.

Although the disclosure has been described in detail with reference to certain preferred embodiments, variations and modifications exist within the spirit and scope of the disclosure as described and defined in the following claims.

The invention claimed is:

1. An impact detection system comprising:
 a sensing device configured to be operably coupled to a structure of interest and to sense impacts, the sensing device including a layer, and a plurality of measuring portions supported by the layer, each of the measuring portions including an input coupling point and an output coupling point and adapted to conduct an electrical signal from the input coupling point to the output coupling point;
 a measurement system in electrical communication with the measuring portions of the sensing device, the measurement system configured to provide electrical signal inputs to the input coupling points of the sensing device, and configured to measure electrical signal outputs at the output coupling points of the sensing device;
 a damage detection processing system operably coupled to the measurement system, the processing system configured to determine data on a damage event from the sensed impact based on changes between the electrical signal inputs at the input coupling points and the electrical signal outputs at the output coupling points, the data including a location of the damage event on the sensing device and a damage event origination axis directed to the point of origin of the ballistic impact; and
 a user interface operably coupled to the damage detection processing system, the user interface including a plurality of visual indicators, the visual indicators including a plurality of light sources arranged in vertically spaced rows, each of the vertically spaced rows including a plurality of horizontally spaced light sources;
 wherein the light sources are arranged in a plurality of vertically spaced annular bands, each annual band including a plurality of circumferentially spaced light sources.

2. The impact detection system of claim 1, wherein illumination of light sources within different bands provides for an indication of elevation of the damage event origination axis.

3. The impact detection system of claim 1, wherein illumination of light sources within the same band provides for an indication of the azimuth of the damage event origination axis.

4. An impact detection system comprising:
 a sensing device configured to be operably coupled to a structure of interest and to sense impacts, the sensing device including a layer, and a plurality of measuring portions supported by the layer, each of the measuring portions including an input coupling point and an output coupling point and adapted to conduct an electrical signal from the input coupling point to the output coupling point;
 a measurement system in electrical communication with the measuring portions of the sensing device, the measurement system configured to provide electrical signal inputs to the input coupling points of the sensing device, and configured to measure electrical signal outputs at the output coupling points of the sensing device;
 a damage detection processing system operably coupled to the measurement system, the processing system configured to determine data on a damage event from the sensed impact based on changes between the electrical signal inputs at the input coupling points and the electrical signal outputs at the output coupling points, the data including a location of the damage event on the sensing device and a damage event origination axis directed to the point of origin of the ballistic impact; and
 a user interface operably coupled to the damage detection processing system, the user interface including a plurality of visual indicators, the visual indicators including a plurality of light sources arranged in vertically spaced rows, each of the vertically spaced rows including a plurality of horizontally spaced light sources;
 wherein the light sources are arranged in first and second circumferentially spaced columns.

5. The impact detection system of claim 4, wherein illumination of light sources within different bands provides for an indication of elevation of the damage event origination axis.

6. The impact detection system of claim 4, wherein illumination of light sources within the same band provides for an indication of the azimuth of the damage event origination axis.

* * * * *